US010537887B2

(12) United States Patent
Hahn et al.

(10) Patent No.: US 10,537,887 B2
(45) Date of Patent: *Jan. 21, 2020

(54) ADSORBENT COMPOSITION AND USE THEREOF

(71) Applicants: BOEHRINGER INGELHEIM RCV GMBH & CO KG, Vienna (AT); SANDOZ AG, Basel (CH)

(72) Inventors: Rainer Hahn, Vienna (AT); Alois Jungbauer, Vienna (AT); Alexandru Trefilov, Munich (DE); Moritz Imendoerffer, Vienna (AT)

(73) Assignees: BOEHRINGER INGELHEIM RCV & GMBH CO KG, Vienna (AT); SANDOZ AG, Basel (CH)

( * ) Notice: Subject to any disclaimer, the term of this patent is extended or adjusted under 35 U.S.C. 154(b) by 740 days.

This patent is subject to a terminal disclaimer.

(21) Appl. No.: 14/913,333

(22) PCT Filed: Aug. 25, 2014

(86) PCT No.: PCT/EP2014/068014
§ 371 (c)(1),
(2) Date: Feb. 19, 2016

(87) PCT Pub. No.: WO2015/025062
PCT Pub. Date: Feb. 26, 2015

(65) Prior Publication Data
US 2016/0193598 A1    Jul. 7, 2016

(30) Foreign Application Priority Data
Aug. 23, 2013  (EP) .................... 13181537
Aug. 23, 2013  (EP) .................... 13181540

(51) Int. Cl.
*B01J 39/20*   (2006.01)
*B01J 39/04*   (2017.01)
*C12N 9/02*    (2006.01)
*C07K 1/18*    (2006.01)
*B01J 39/26*   (2006.01)
*B01J 41/14*   (2006.01)
*B01J 41/20*   (2006.01)
*B01J 47/04*   (2006.01)
*B01D 15/36*   (2006.01)
*C07K 14/435*  (2006.01)
*C07K 16/00*   (2006.01)
*B01J 39/05*   (2017.01)
*B01J 39/07*   (2017.01)
*B01J 41/05*   (2017.01)
*B01J 41/07*   (2017.01)

(52) U.S. Cl.
CPC ............ *B01J 39/20* (2013.01); *B01D 15/362* (2013.01); *B01D 15/363* (2013.01); *B01J 39/04* (2013.01); *B01J 39/05* (2017.01); *B01J 39/07* (2017.01); *B01J 39/26* (2013.01); *B01J 41/05* (2017.01); *B01J 41/07* (2017.01); *B01J 41/14* (2013.01); *B01J 41/20* (2013.01); *B01J 47/04* (2013.01); *C07K 1/18* (2013.01); *C07K 14/43595* (2013.01); *C07K 16/00* (2013.01); *C12N 9/0089* (2013.01); *C12Y 115/01001* (2013.01)

(58) Field of Classification Search
CPC ...... B01D 15/362; B01D 15/363; B01J 39/04; B01J 39/05; B01J 39/07; B01J 39/20; B01J 39/26; B01J 41/05; B01J 41/07; B01J 41/14; B01J 41/20; B01J 47/04; C07K 14/43595; C07K 16/00; C07K 1/18
USPC ........ 252/184; 424/489, 184.1, 204.1, 234.1, 424/265.1, 277.1, 278.1, 283.1, 450, 688, 424/426, 490, 491, 493, 497, 93; 502/159; 525/54.2; 435/375, 455, 173.9, 435/325, 7.25, 173.1, 176, 239, 29, 34, 435/456
See application file for complete search history.

(56) References Cited

U.S. PATENT DOCUMENTS 4,169,804 A  * 10/1979 Yapel, Jr. ............. A61K 9/5094
                                                    252/62.53
2011/0003367 A1   1/2011 Tajima et al.
2016/0270012 A1   9/2016 Chen et al.

FOREIGN PATENT DOCUMENTS

JP         2009-247244         10/2009
WO     WO 2015/025062 A1       2/2015

OTHER PUBLICATIONS

Ono et al. "Flocculation and retention of precipitated calcium carbonate by cationic polymeric microparticle flocculants", Journal of Colloid and Interface Science Apr. 1, 1997 US, vol. 188, No. 1, Apr. 1, 1997 (Apr. 1, 1997), pp. 183-192. (Cited on International Search Report). (Year: 1997).*
JP, 2016-535504 Office Action, dated Sep. 4, 2018.
WO, PCT/EP2014/068014 ISR and Written Opinion, dated Oct. 29, 2014.
Fisher, S., et al., "Effect of Cross-Linking on the Properties of Carboxylic Polymers. I. Apparent Dissociation Constants of Acrylic and Methacrylic Acid Polymers", J. Phys. Chem., 1956, vol. 60, No. 8, pp. 1030-1032.

(Continued)

*Primary Examiner* — Janet L Epps-Smith
(74) *Attorney, Agent, or Firm* — One LLP

(57) ABSTRACT

The present invention provides a novel adsorbent composition for recovering biomolecules from a fluid. The composition comprises positively and negatively charged microparticles in the form of ground particles. The adsorbent is particularly useful for purification of biomolecules from the cell culture.

18 Claims, 18 Drawing Sheets

(56) References Cited

OTHER PUBLICATIONS

Figure 1A:
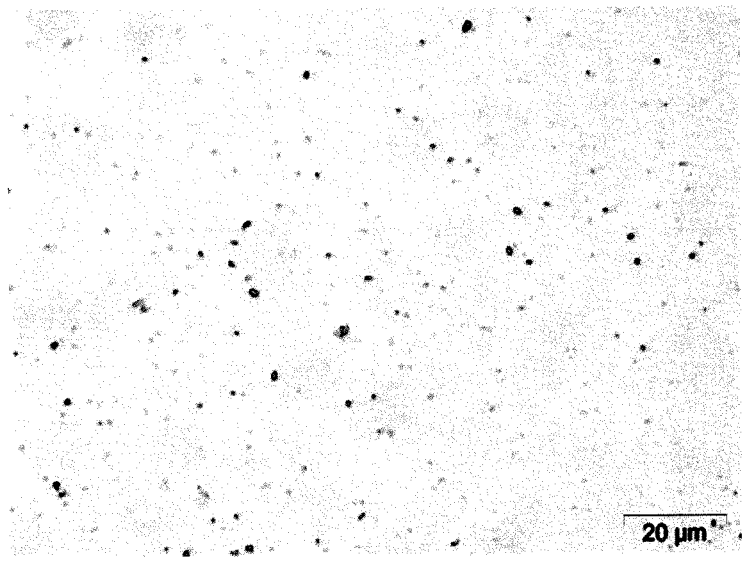

Przybycien, T. M., "Alternative bioseparation operations: life beyond packed-bed chromatography", Current Opinion on Biotechnology, 2004, vol. 15, No. 5, pp. 469-478.
Devolder et al., "Three Dimensionally Flocculated Proangiogenic Microgels for Neovascularization," Journal of Biomaterials, 2010, pp. 6494-6501, No. 31.
Ono et al., "Flocculation and Retention of Precipitated Calcium Carbonate by Cationic Polymeric Microparticle Flocculants," Journal of Colloid and Interface Science, 1997, pp. 183-192, No. 188.
Paril et al., "Adsorption of pDNA on microparticulate charged surface," Journal of Biotechnology, 2009, pp. 47-57, No. 141.
Xiao et al., "Synergetic Effect of Cationic Polymer Microparticles and Anionic Polymer on Fine Clay Flocculation," Journal of Colloid and Interface Science, 1999, pp. 409-417, No. 216.

* cited by examiner

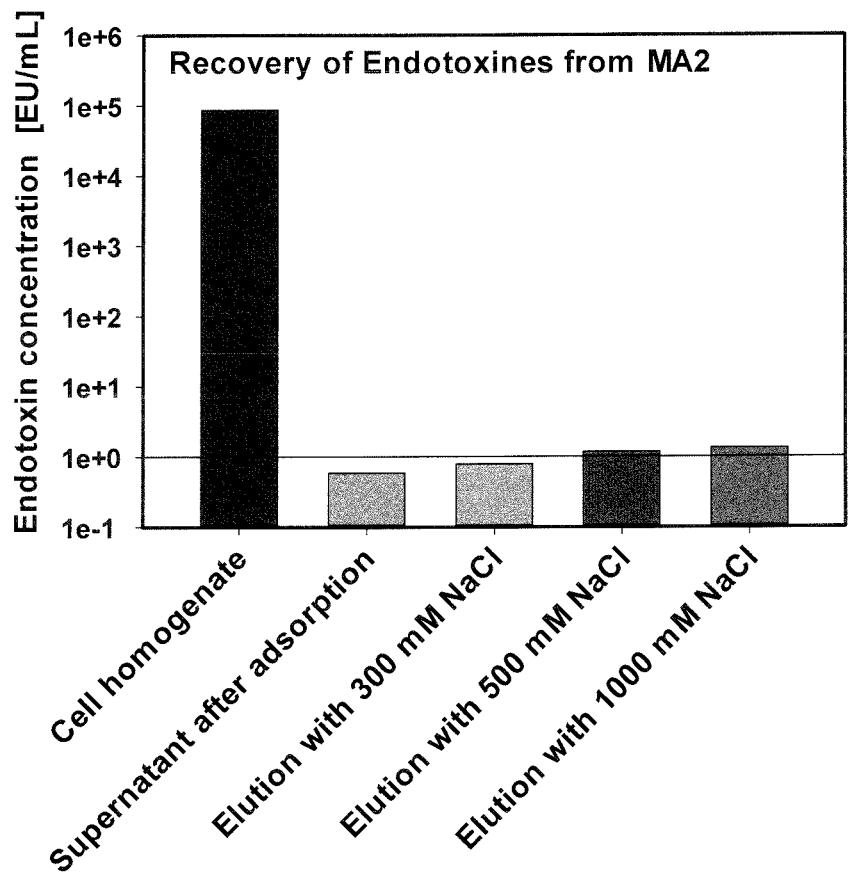
Fig. 12
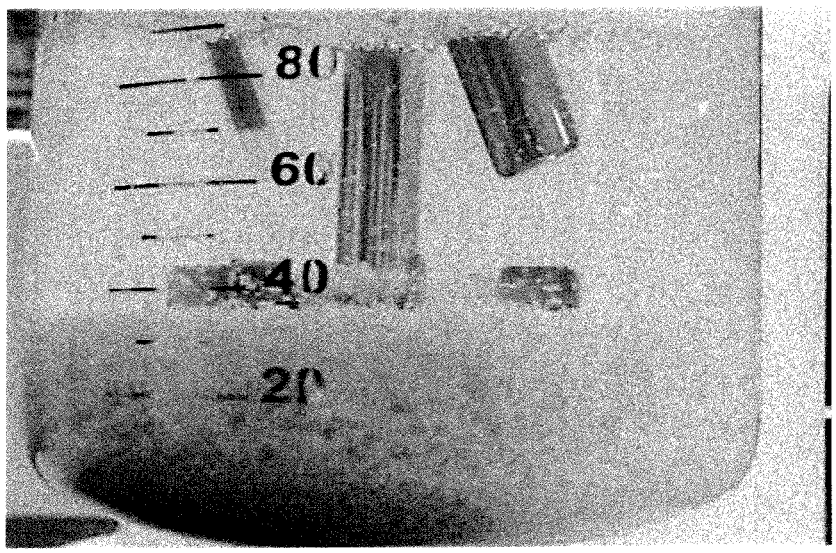
Fig. 13.1

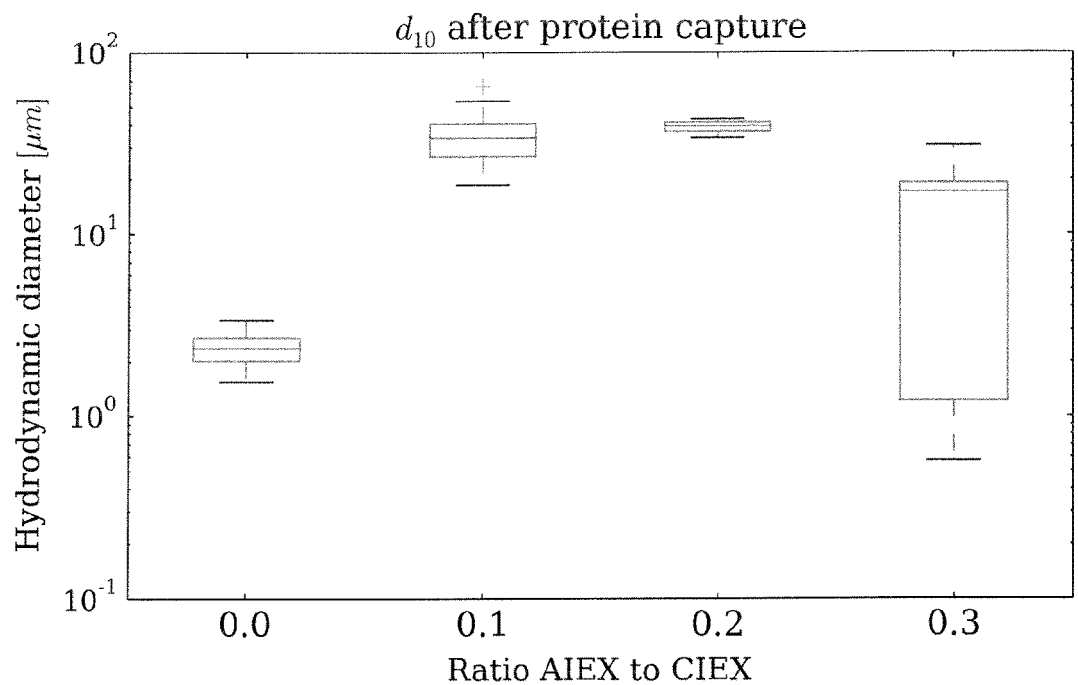
Fig. 13.2
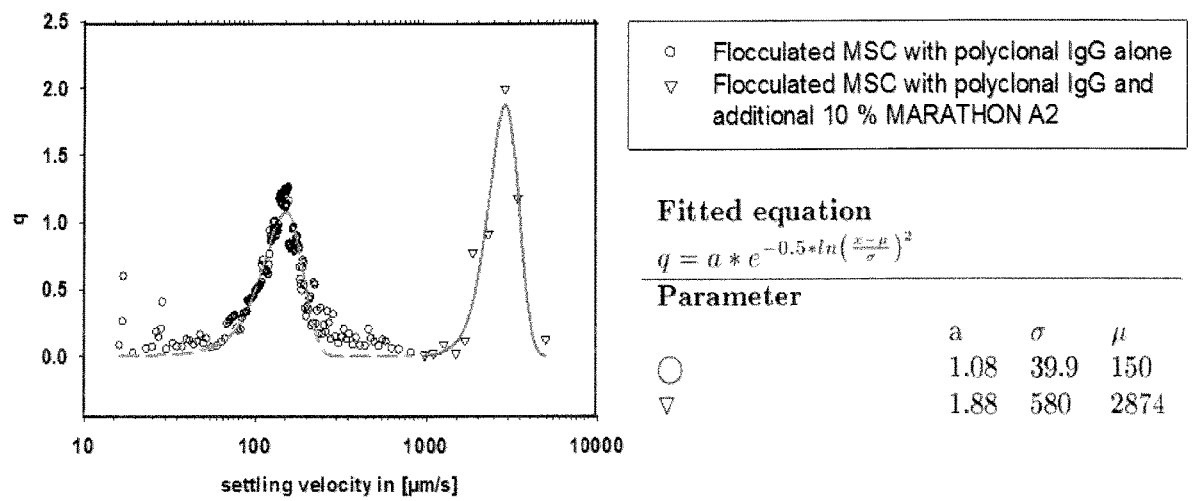
Fig. 14.1

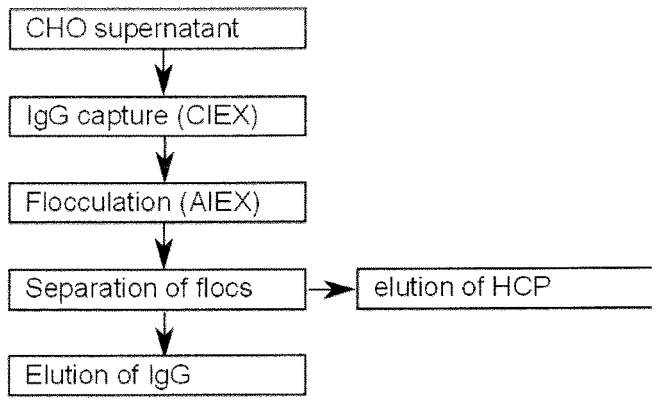
Fig. 14.2
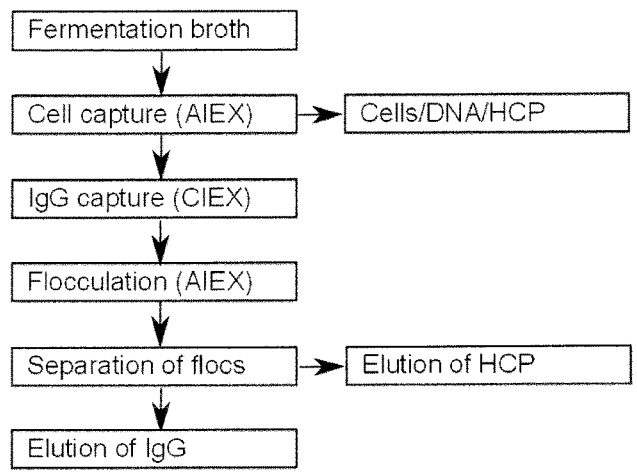
Fig. 14.3
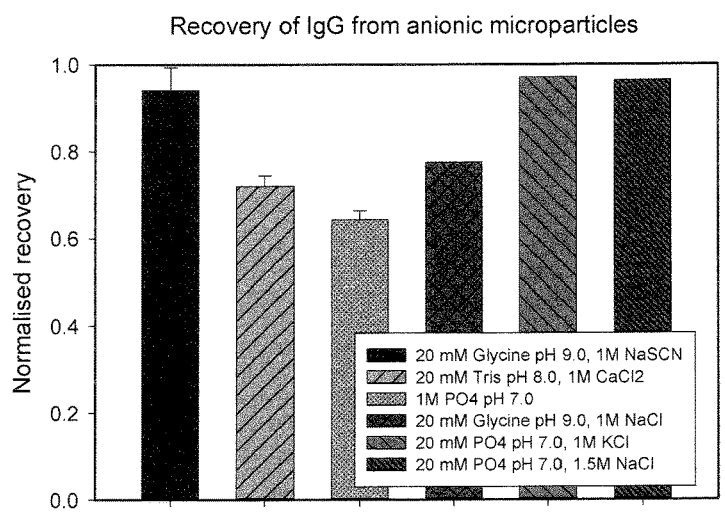
Fig. 14.4

ADSORBENT COMPOSITION AND USE THEREOF

FIELD OF INVENTION

The present invention generally relates to the field of separation of biomolecules from a fluid, in particular, from a biological fluid. The present invention is related to compositions, uses and methods applied for the recovery of biomolecules from a biological fluid. Furthermore, in another aspect, the present invention is related to the field of cell culture and purification of biomolecules from the cell culture.

BACKGROUND OF THE INVENTION

Separation of biomolecules from a mixture has traditionally been performed by utilizing chromatographic techniques, filtration or precipitation. The continuing surge in the development of biotechnology products and processes has brought with it the need for efficient and cost effective separation and purification processes and apparatus. The preparation of biomolecules by fermentation processes can be divided into two general categories which are generally referred to as "upstream" and "downstream" processes. The upstream processes address the biochemical design of the system to produce the desired biopharmaceutical product and the downstream processes focus on harvesting and purifying the final product.

Downstream processing typically involves (1) the release of the contents of the fermentation cells, if necessary, for example by cell disruption, since the fermentation product, e.g. a protein or polynucleotide, such as a plasmid, may already be in the culture supernatant because of secretion by the host cell; (2) centrifugation to provide clarification of the contents, typically by separating the cell debris from the mother liquor which contains the desired product and other biological entities; (3) ultrafiltration to concentrate the mother liquor for subsequent steps; and (4) final product purification, typically by liquid chromatographic techniques using multi-method separation methods, e.g., ion exchange, hydrophobic interaction, reverse phase.

Chromatography resins used for protein adsorption generally comprise macroporous, hydrophilic materials. In traditional chromatographic techniques conventional granular chromatography materials that have defined particle and pore sizes are used. Porosity is essential to provide sufficient surface area for high capacity, while hydrophilic surfaces enable reversible adsorption. Base materials for chromatographic resins are usually cross-linked natural polymers, like cellulose, dextran or agarose, as well as synthetic polymers made of polyacrylamide, polymethacrylate and polystyrene divinylbenzene derivatives. The latter is often coated with a hydrophilic polymer. Ion exchange resin, hydrophobic interaction resin or affinity resins are coupled with functional ligands by chemical derivatization or by surface grafting technologies.

In the industry, upstream manufacturing capacities have increased dramatically, with many manufacturers choosing to operate several 10000 L bioreactors simultaneously. However, standard chromatography methods do not allow rapid scale-up.

At the first stage of a chromatographic purification step (also called the capture step), due to the large sample volume that has to be processed, large bed volumes are generally used. However, large columns suffer from scale-related packing problems such as hysteresis, edge-effects and resin compression, which result in unpredictable fluid distribution and pressure drops.

The performance of packed chromatography columns in industrial and preparative applications is limited by the maximum allowable pressure drop. Due to the pressure drop restrictions, resin beads with larger diameter such as larger than 40 µm are used.

The capturing of the biomolecules relies on pore diffusion, but large biomolecules do not readily diffuse into the pores, and the diffusional pathway is increased with the use of larger resin particles. This causes mass transfer resistance and lowers the column efficiency, because large molecules can only bind to the outer surface of the resin bead. Therefore, longer residence time is required to find binding ligands inside the resin particles, which in turn leads to a slow adsorption process. Since high throughput is very important for processing large sample volumes, the use of large particles, in particular for the adsorption of large proteins, has an impact on the overall productivity.

In sum, current chromatographic techniques cannot be easily scaled up to meet the demands in industry. The methods suffers from the drawbacks of being time consuming and expensive to practice in industrial scale.

Accordingly, there is a need to provide alternatives to column chromatography. Methods alternative to chromatography include membrane filtration, aqueous two-phase extraction, precipitation, crystallization, monoliths and membrane chromatography have been proposed (Przybycien et al "Alternative bioseparation operations: life beyond packed-bed chromatography" *Curr Opin Biotechnol.* 2004; 15(5):469-78).

Paril et al. *J. Biotechnol.* 2009; 141: 47-57 provide a means and methods for adsorption of pDNA on microparticulate charged surface. Specifically, Paril et al. uses polystyrene based microparticles provided by Rohm and Haas to adsorption of pDNA. However, Paril et al. does not teach how to prepare these microparticles such that they were able to adsorb pDNA. Generally, microparticles refer to particles having micron size.

There is still a need to provide an alternative, preferably improved methods for obtaining biomolecules from a fluid alternative to standard chromatographic techniques. The technical problem of the invention is to comply with one or more of the above mentions needs.

\*\*\*

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", or and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

SUMMARY

The present invention provides a novel process and adsorbent material which allow the direct capture of molecules, preferably biomolecules from, e.g., liquids, fluids such as culture supernatant, from cell homogenates and/or other biological fluids. The present invention is easy, fast and cheap compared to traditional chromatographic techniques. As described earlier, current capture of biomolecules is made by either adsorption on fixed beds packed with porous particles or by batch adsorption with porous particles. However, these processes have undesired drawbacks, since large bed volumes of columns are required which in turn leads to slow adsorption because of long diffusional pathways in the pores of the particles having usually a large diameter. Moreover, these processes are mass transfer limited.

In accordance with the invention, a novel adsorbent material for the capture of biomolecules is provided. The adsorbent material comprises microparticles which are solid and charged. The microparticles are in ground form and can be prepared by grinding anion-exchange resin and cation exchange resin.

The present invention also provides as a novel adsorbent material for the capture of biomolecules microparticles which are solid and hydrophobic. The microparticles are in ground form and can be prepared by grinding hydrophobic adsorbent material such as AMBERLITE® XAD4, AMBERLITE® XAD7HP, AMBERLITE® XAD761.

Fine particles with rough surfaces as provided by the invention are not used as chromatography media in packed beds because they plug frits and filters and therefore lead to processing difficulties. Furthermore, they extend settling times in batch processing applications and contribute to resin attrition. However, despite these discouraging assumptions based on common general knowledge, the inventors have surprisingly found that the particles of the invention are able to adsorb molecules, preferably biomolecules, in particular polypeptides, rapidly and highly efficiently, making them suitable for batch adsorption. Furthermore, it has been found that the invention exhibits fast adsorption. In particular, the inventors found that the particles, both the charged and hydrophobic particles of the invention flocculate upon binding to molecules, preferably biomolecules. The formation of flocs enables the easy separation of the biomolecule from the biological fluid including unwanted cell debris. Therefore, the adsorbent in the present invention can be utilized to adsorb molecules, preferably biomolecules in a scalable manner. Furthermore, it has been surprisingly found that using charged particles in the process of recovery has high, adsorption capacity. Additionally, it also allows easily handling of the flocs formed therefrom as well as the easy separation of formed flocs from the fluid.

In addition, the inventors have discovered that the microparticles can also act to disrupt the cell structure. Therefore, the present invention in one aspect provides a simplified use and method in which the steps of cell disruption and recovery of the biomolecules in the downstream processing are combined.

The term "cell disruption" or "disruption of cells" are used interchangeably and generally refer to methods or processes for interrupting cellular integrity. Cell disruption as used herein includes, but is not limited to, a method or process for making a cell permeable to such an extent that biomolecules are released from the cell. Cell disruption may or may not involve cell death. Preferably, cell disruption does not involve complete fragmentation of cellular structures. Without wishing to be bound by a specific theory, it is assumed that a decrease of cell fragmentation reduces the level of (potentially) contaminating cell debris. In some embodiments of the invention, cells are disrupted by the method described herein and release biomolecules, but remain viable. The released biomolecules may or may not adsorb to the microparticles used to disrupt cells. The released biomolecules can subsequently be recovered from the biological fluid using the methods described herein or other known techniques. Thus, the present invention offers a novel method for cell disruption, biomolecule release and subsequent biomolecule recovery in a simplified two-step process. Microparticles of the present invention may be used to open up the cell to release biomolecules so that they could be recovered in the cell suspension, irrespective of the acidity of the biomolecules (i.e. the biomolecule may be acidic, basic or neutral).

According to the first aspect of the invention, the composition comprises positively charged microparticles and negatively charged microparticles, wherein the positively charged microparticles comprise ground polymeric anion-exchange resin, and wherein the negatively charged microparticles comprise ground polymeric cation exchange resin. The composition refers to positively charged microparticles and negatively charged microparticles that are mixed or not mixed with each other. As will appear in the present specification, the adsorbent material can be used by adding positively charged microparticles and negatively charged microparticles separately into the biological fluid. Alternatively, they can be pre-mixed and added to the biological fluid.

In a second aspect of the invention, the composition comprises hydrophobic microparticles. These hydrophobic microparticles are capable of adsorbing in particular peptides or polypeptides. The mechanism for adsorption is thought to be based primarily on hydrophobic (Van der Waals, London Type) attractions between the hydrophobic portions of the adsorbed ligands such as peptides or polypeptides and the polymeric surface of the microparticles.

The microparticles are obtainable (can be obtained) by grinding resin as described herein, for example, by grinding ion-exchange resin and optionally conditioning the resin. Such particles are preferably referred to herein as "microparticles," "adsorbent particles", "adsorbent", "particles", "ground particles", or "ground resin" in the present invention. These terms are used interchangeably. Preferably, the microparticles are obtained by grinding conventional large-diameter small-pore particles which are usually intended, e.g., for water de-ionization and waste water treatment.

The positively charged microparticles preferably comprise ground polymeric anion-exchange resin and the negatively charged microparticles preferably comprise ground polymeric cation exchange resin. The microparticles in a preferred embodiment are in the form of a powder or present in a liquid medium forming a particle suspension. Preferably, the microparticles are not in a form of an aqueous gel. A composition comprising both positively charged microparticles and negatively charged microparticles can be prepared by mixing positively charged microparticles and negatively charged microparticles. They could be prepared by providing positively charged microparticles and negatively charged microparticles separately so they are added separately into the biological fluid.

The cation exchange resin can be used to prepare the negatively charged microparticles. The cation exchange resin can be weakly or strongly acidic. Likewise, anion-exchange resin can be used to prepare the positively charged microparticles. The anion-exchange resin can be weakly or strongly basic.

The ion-exchange resin according to the present invention can be based on any suitable material. Preferably, the resin is polystyrene-based, Hydroxyethyl methacrylate (HEMA)-based, dimethylamino ethylmethacrylate (DMAEMA)-based, dimethylamino ethylmethacrylate (pDMAEMA) based, polyacrylamide based or methacrylic acid (MAA) based. More preferably, the resin is polystyrene cross-linked with divinylbenzene-based.

In one preferred embodiment, the microparticles are in the form of ground particles having an average particle size less than about 10 μm, such as less than about 5 μm. Microparticles of ~1 μm diameter (d50) of the present invention do have a similar protein capacity to spherical nanoparticles with ~100 nm diameter (d50) based on calculated surface area, measured protein capacity, and theoretical calculations assuming a hexagonal footprint of a globular protein. More preferably, the microparticles of the present invention have a specific area comparable, i.e. being equivalent to macroporous media having high binding capacity such as the particles of Nuvia media (Nuvia S Media—online Catalog 2013, No. 156-0311, Nuvia Q Media—online Calalog 2013, No. 156-0411, or Nuvia cPrime media—online Catalog 2013 No. 156-3401) developed by Bio-Rad Laboratories (USA). By "specific area" the area per milliliter (ml) of slurry or the area per gram (g) of resin is meant.

Microparticles according to the present invention can be obtained by grinding anion-exchange resin and cation exchange resin. Anion-exchange resin may be, for example, AMBERLITE® IRA-485, AMBERLITE® IRA-400, DOWEX® 1X2-100, DOWEX® 1-8-100, DIAION® SA 20A, DOWEX® MARATHON® A2 or other cation-exchange resin known in the art, and cation exchange resin may be, for example, AMBERLITE® IRC-748, DOWEX® 50 WX2-100, DOWEX® 50 WX8-100, DIAION® SK 110, DOWEX® MARATHON® MSC, or other anion-exchange resin known in the art.

The ratio of positively charged microparticles and negatively charged microparticles can range from about 0.1:99.9 (w/w) to 99.9:0.1 (w/w).

In another aspect, the invention provides the use of the positively charged microparticles and negatively charged microparticles disclosed herein to adsorb biomolecules, preferably proteins or polynucleotides, such as DNA, e.g. plasmid DNA, from a fluid. In the alternative, hydrophobic microparticles are used for the same purpose. Further biomolecules that can be adsorbed by the microparticles of the present invention are described herein below. The fluid is a biological fluid such as cell homogenate, fermentation supernatant, cell suspension, fermentation broth, etc. A more detailed and also preferred description of "biological fluid" as well as preferred examples of biological fluids is provided herein below.

Yet another aspect of the invention is the use of the microparticles, particularly the use of charged microparticles to disrupt the cell and to adsorb biomolecules released from the cells. Such cells are preferably contained in a cell suspension, a fermentation broth or culture broth as described herein.

The present invention is also related to a method of obtaining biomolecules from a biological fluid, such as cell homogenate or fermentation supernatant, comprising adding the adsorbent described herein; allowing the microparticles to form flocs; removing the flocs from the biological fluid, and recovering the biomolecules by desorbing the biomolecules from the flocs or purifying the biomolecules from the biological fluid.

Preferably, the method is used to obtain biomolecules from a fermentation broth, fermentation supernatant, cell homogenate or cell suspension. In one preferred embodiment, the biological fluid is agitated after the microparticles are added.

Examples of biological fluids include cell cultures and cell homogenates, cell lysates, cell suspensions, fermentation broth, culture broth, fermentation supernatant, culture supernatant, cell supernatants, such as from *E. coli, Pichia pastoris*, and CHO cell culture. The cell cultures and cell homogenates, cell lysates, cell suspensions, fermentation broth, culture broth, fermentation supernatant, culture supernatant, cell supernatants can additionally be filtered, concentrated, dialyzed, conditioned, or treated in any other way. cell cultures and cell homogenates, cell lysates, cell suspensions, fermentation broth, culture broth, fermentation supernatant, culture supernatant, cell supernatants and the like as described herein can be conditioned by, e.g., dilution, pH adjustment, adjustment of salinity, etc. or treated in any other way.

In another aspect, the present invention provides a kit comprising positively charged microparticles and negatively charged microparticles or hydrophobic microparticles. The kit may further include means for suspending the microparticles, such as water.

In addition, the present invention also provides a biological fluid comprising biomolecules and the positively charged microparticles and negatively charged microparticles or hydrophobic microparticles of the present invention.

The exact nature of this invention, as well as its advantages, will become apparent to a skilled person from the following description and examples. The present invention is thus not limited to the disclosed preferred embodiments or examples. A skilled person can readily adapt the teaching of the present invention to create other embodiments and applications.

DRAWINGS BRIEF DESCRIPTION

Figure 1B:
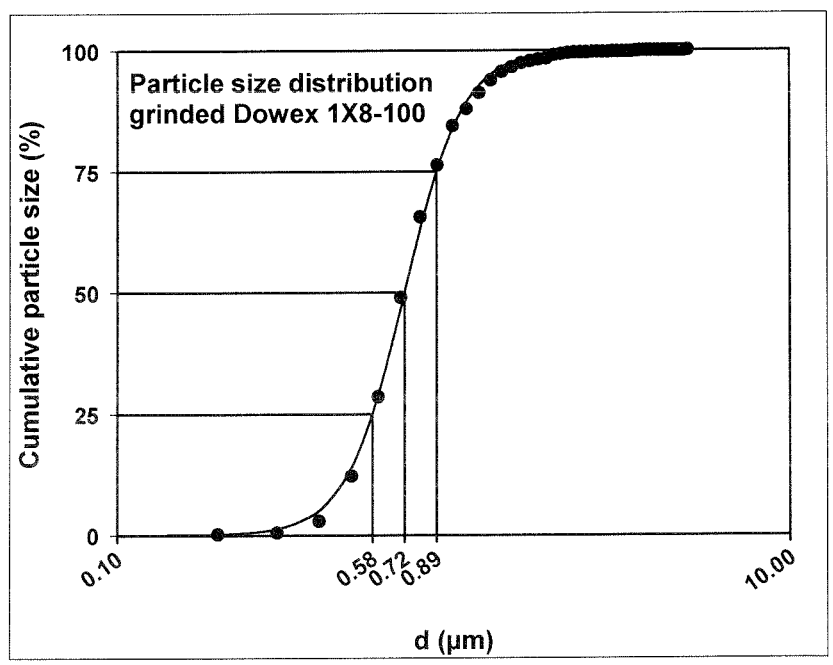

FIG. 1: Light microscopy picture (1000× magnification) (FIG. 1a) and the particle size distribution of microparticles prepared from DOWEX® 1X8-100 (FIG. 1b).

Figure 2:
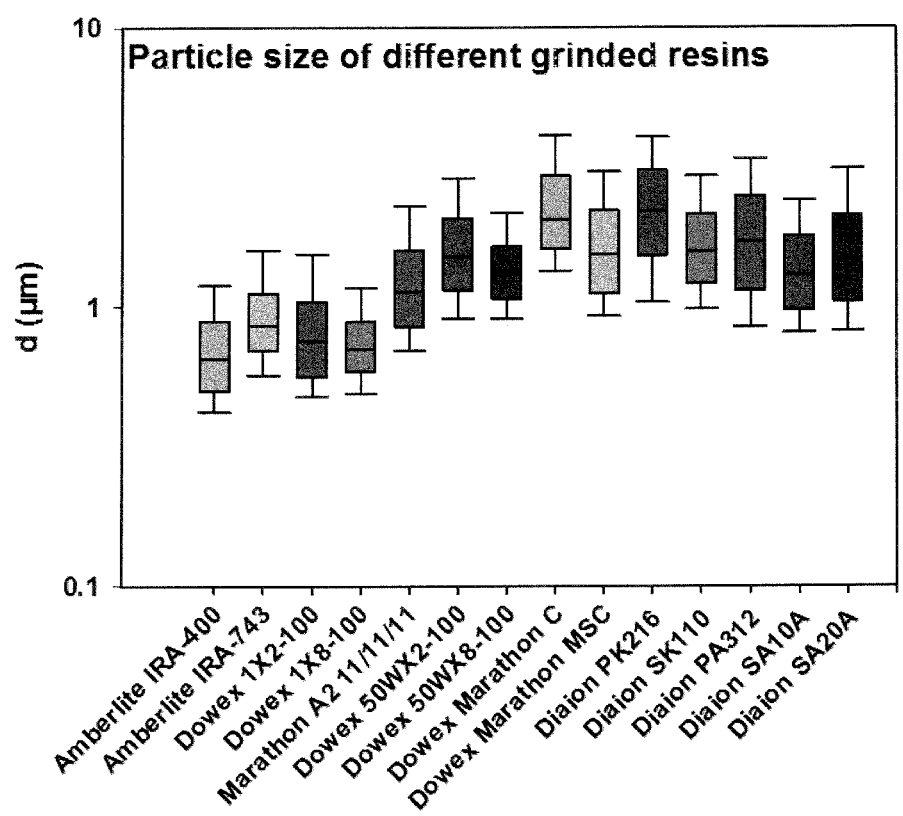

FIG. 2: Particle size distribution of various microparticles.

Figure 3A:
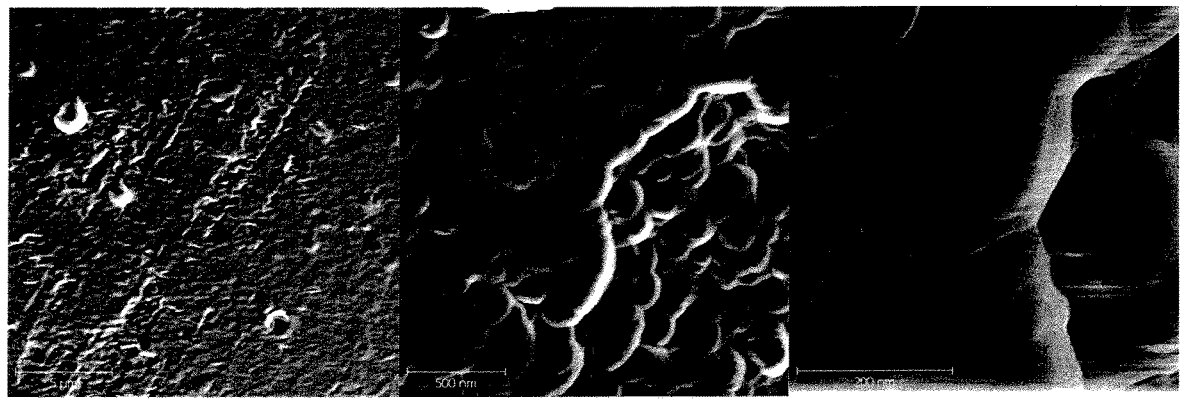
Figure 3B:
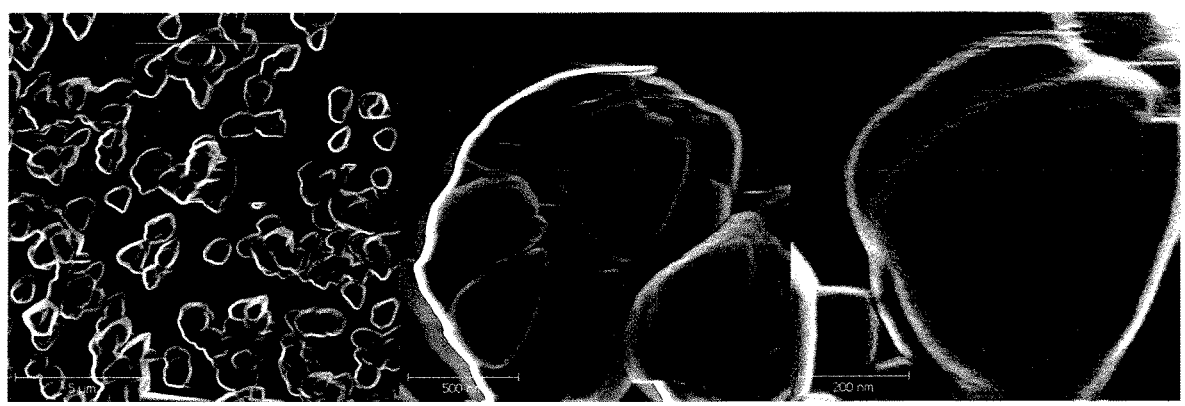

FIG. 3a-b: Atomic force microscopy images of the surface of DOWEX® MARATHON® A2 (before grinding in FIG. 3a and ground FIG. 3b); increasing detail discrimination from left to right.

Figure 3C:
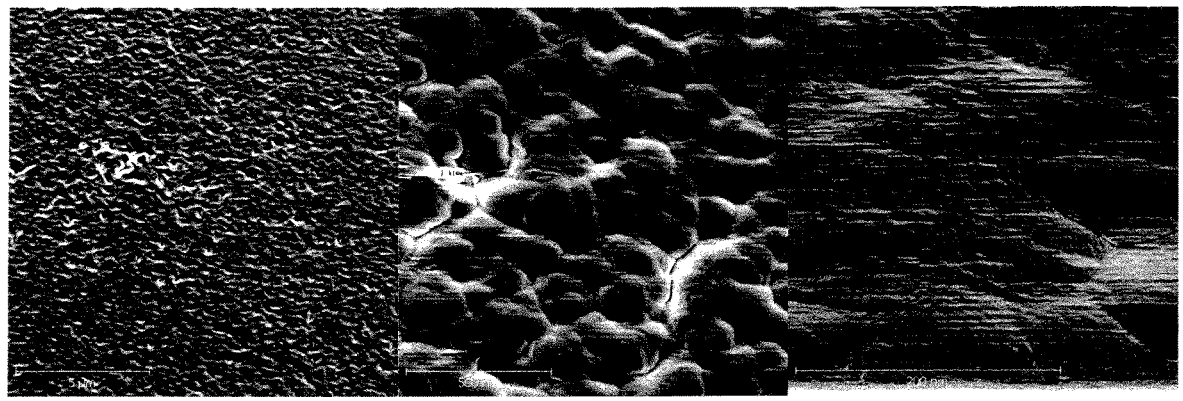
Figure 3D:
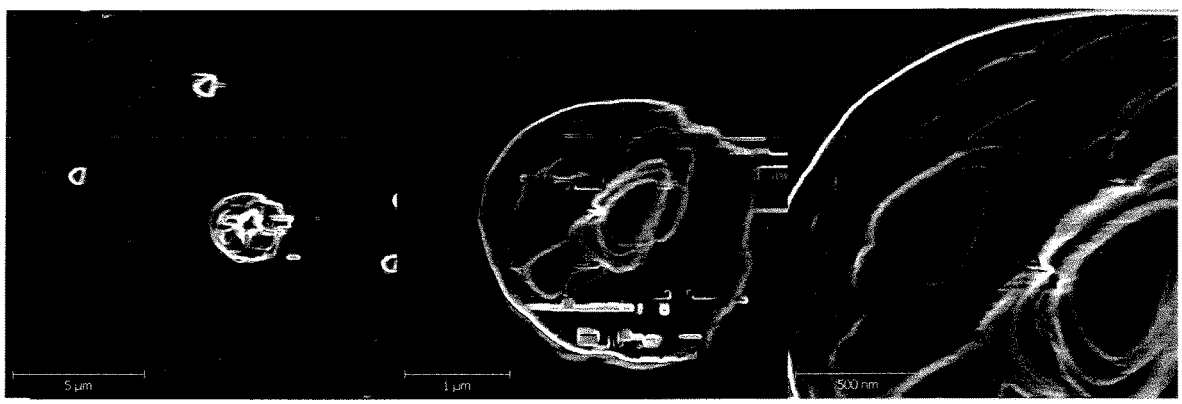

FIG. 3c-d: Atomic force microscopy images of the surface of DOWEX® MARATHON® MSC (before grinding in FIG. 3c and ground FIG. 3d); increasing detail discrimination from left to right.

Figure 4:
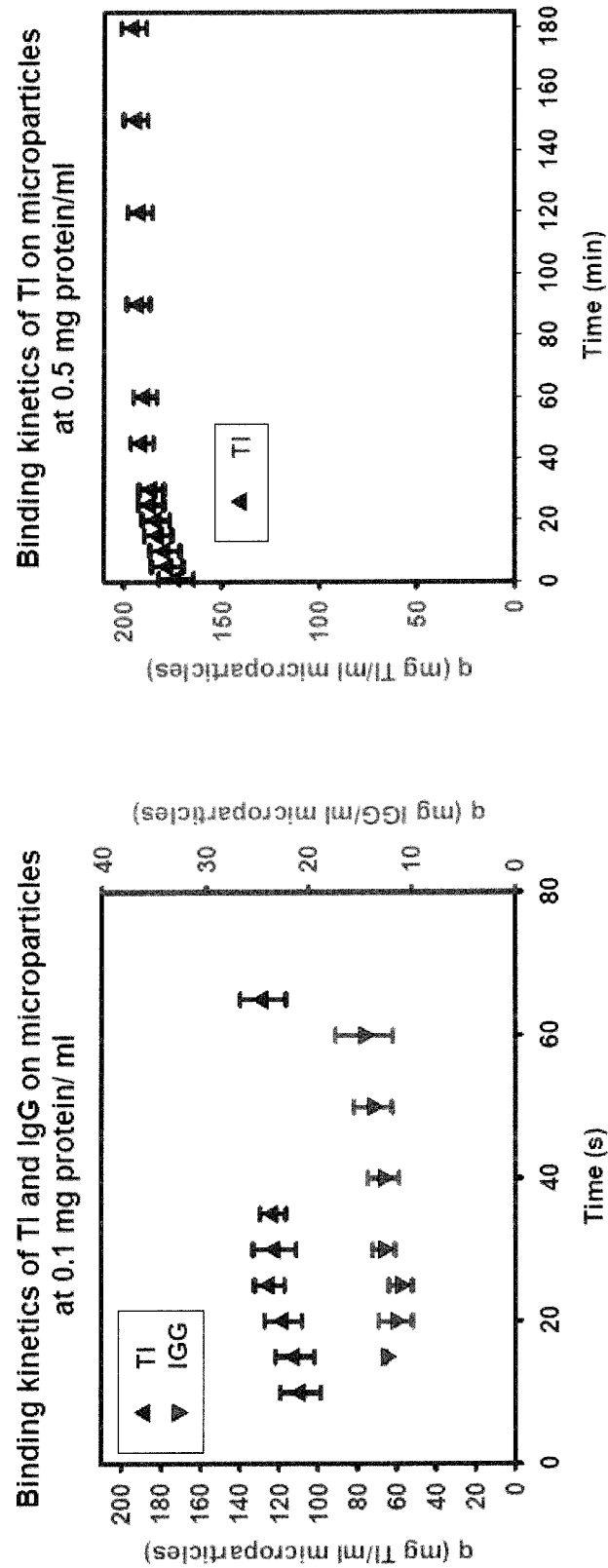

FIG. 4: Adsorption kinetics of Trypsin inhibitor (TI) and IgG on microparticles at a concentration of 0.1 mg/ml (left panel) and of TI at a concentration of 0.5 mg/ml (right panel).

Figure 5B:
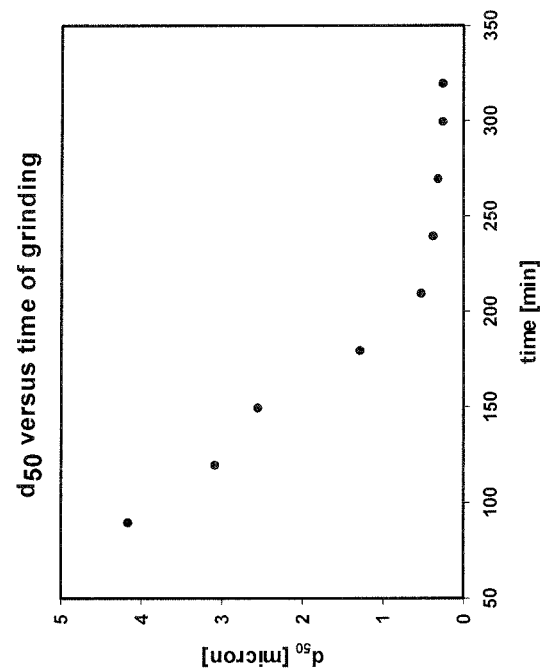
Figure 5A:
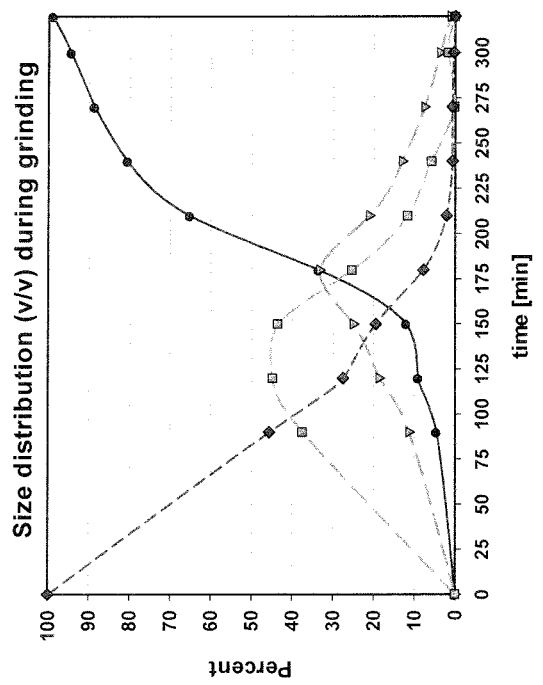

FIG. 5: Size distribution (FIG. 5a) and mean diameter (FIG. 5b) of the microparticles during the grinding process of DOWEX® MARATHON® MSC with a Labstar LS1 mill. Percentage is given as (v/v).

Figure 6B:
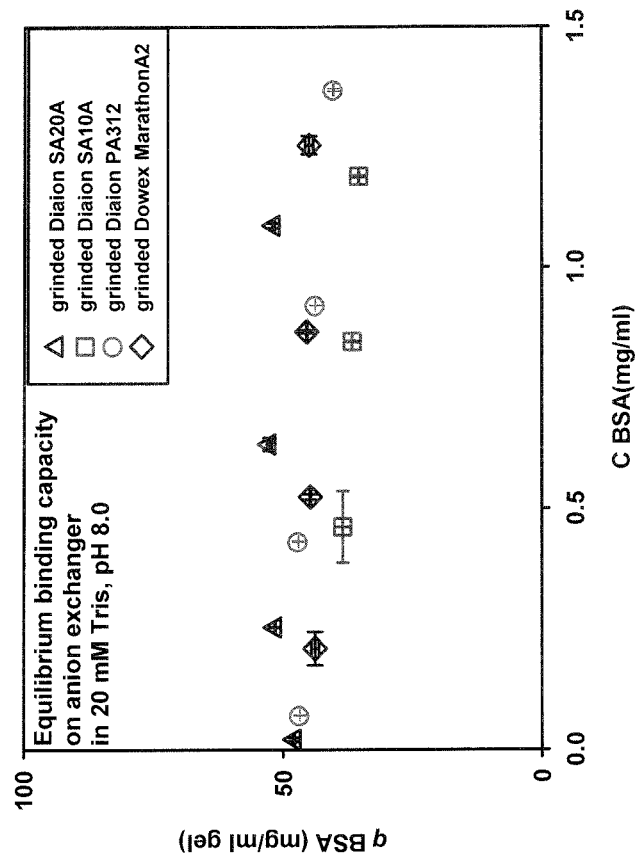
Figure 6A:
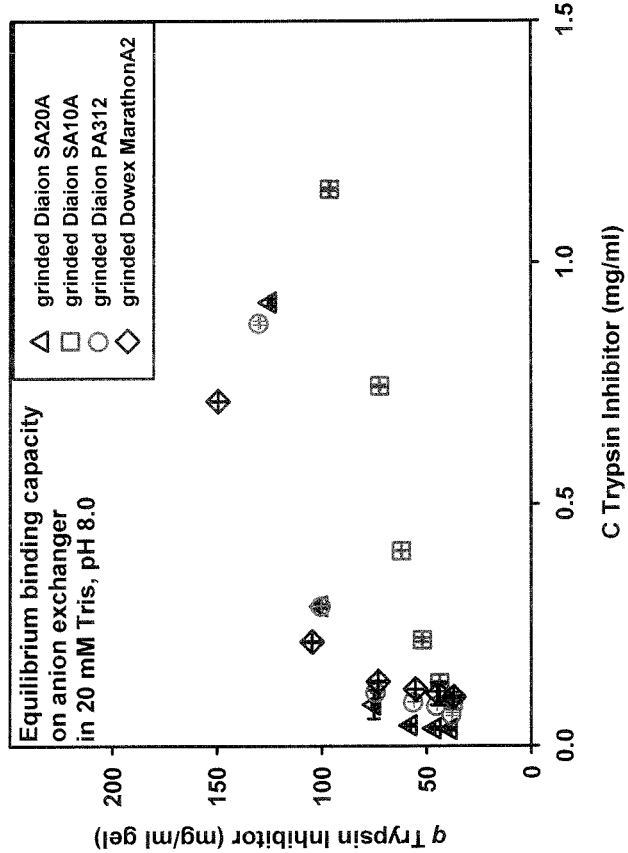

FIG. 6: Equilibrium capacity of trypsin inhibitor (FIG. 6a) and bovine serum albumin BSA (FIG. 6b) on various anion-exchange microparticles. Buffer conditions were 20 mM Tris, pH 8.0. Incubation time was ½ hour.

Figure 7B:
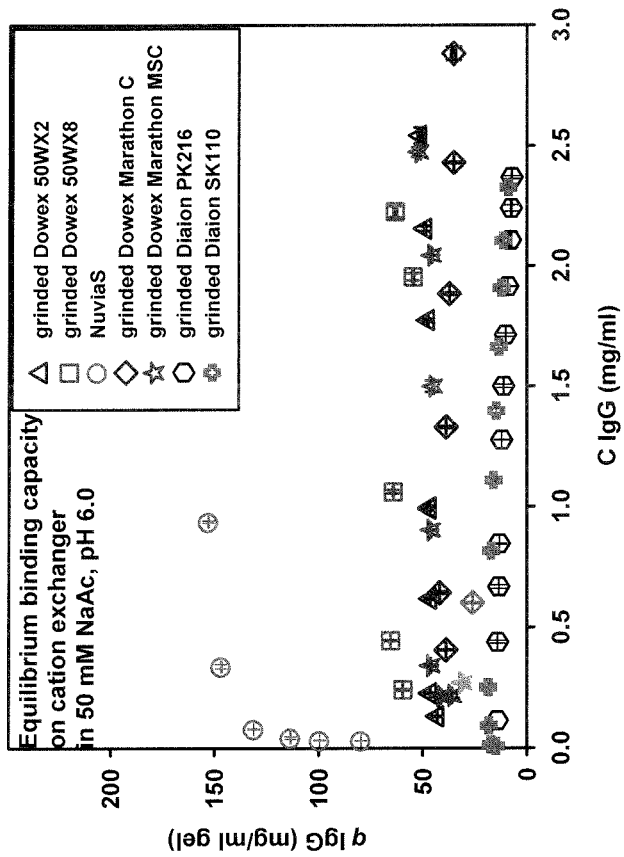
Figure 7A:
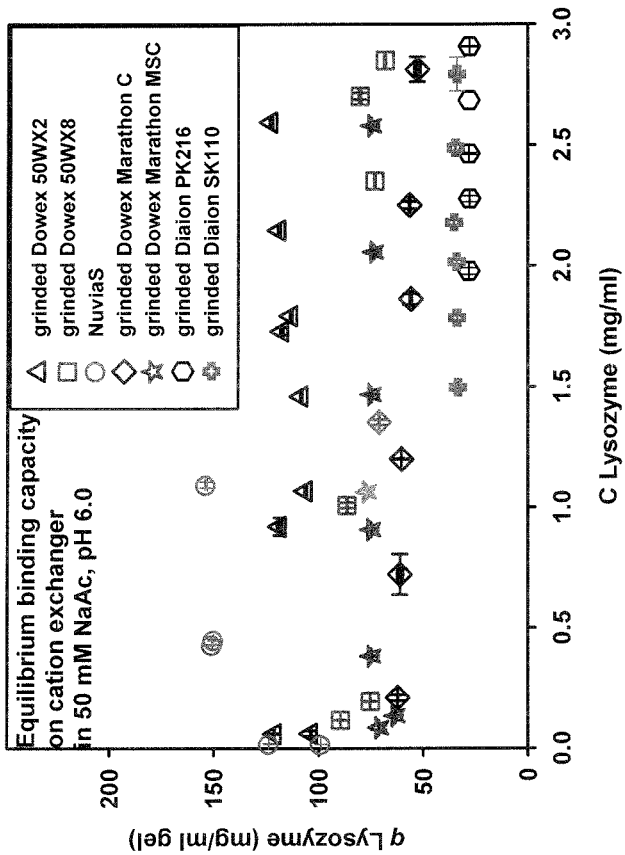

FIG. 7: Equilibrium capacity of lysozyme (FIG. 7a) and polyclonal IgG (FIG. 7b) on various cation exchange microparticles and polymeric particles Nuvia S. Buffer conditions were 50 mM sodium acetate, pH 6.0. Incubation time was ½ hour for micro particles and 12 hours for Nuvia S.

Figure 8:
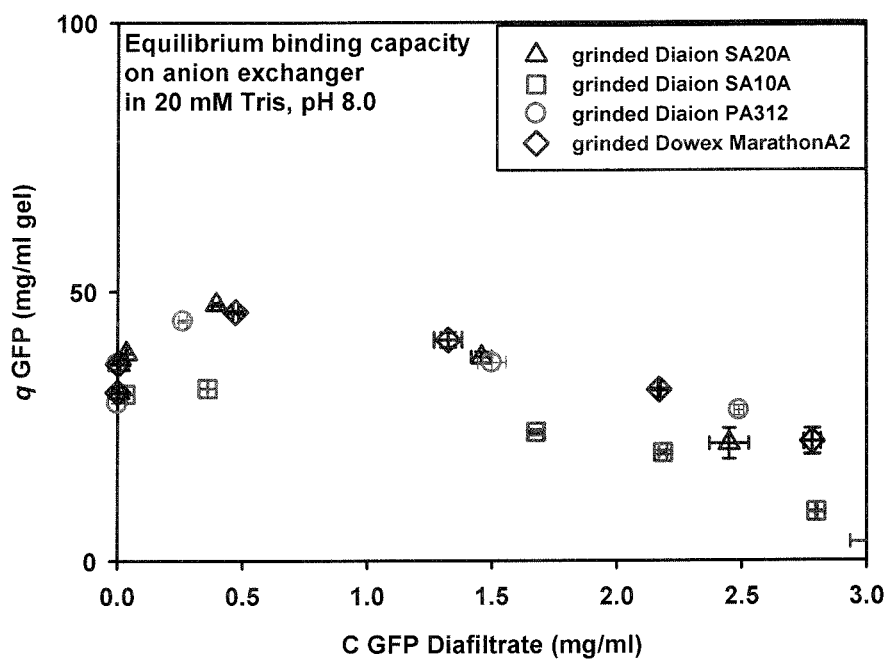

FIG. 8: Equilibrium capacity of GFP from E. coli diafiltrate on anion-exchange microparticles. Buffer conditions were 20 mM Tris, pH 8.0. Incubation time was ½ hour.

Figure 9B:
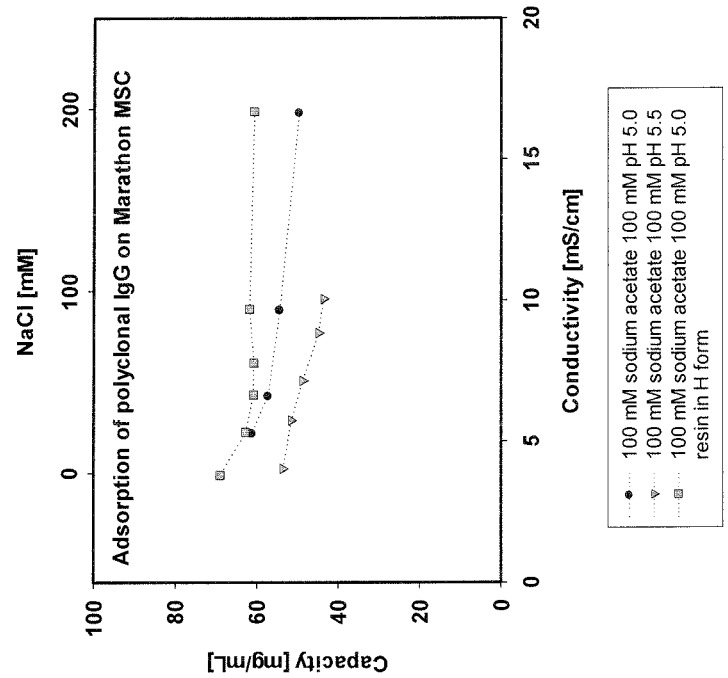
Figure 9A:
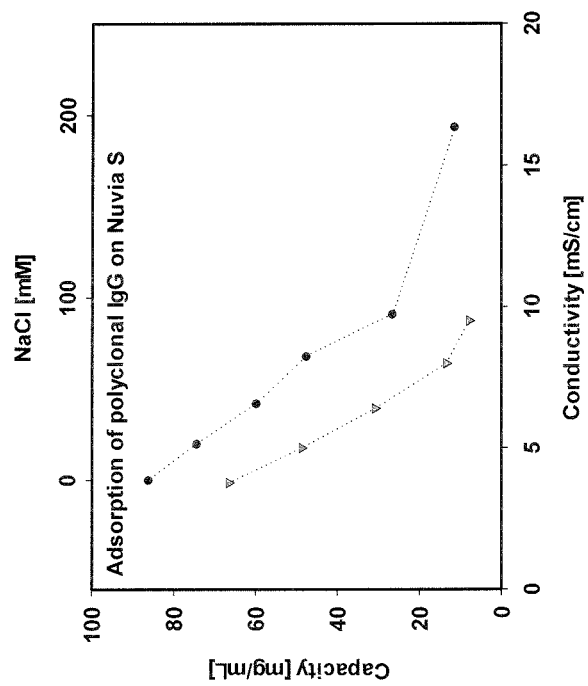

FIG. 9: Equilibrium capacities of polyclonal IgG plotted against the conductivity of the adsorption buffer for NuviaS resin (FIG. 9a) and DOWEX® MARATHON® MSC microparticles (FIG. 9b).

Figure 10:
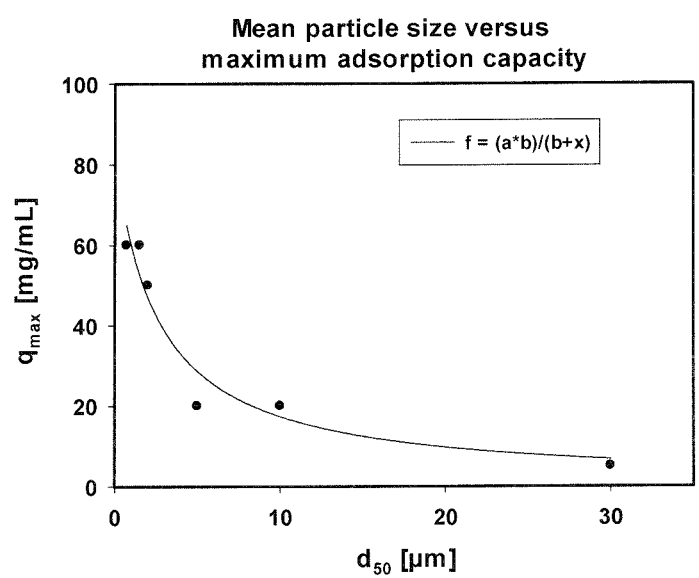

FIG. 10: Equilibrium capacities for polyclonal IgG on DOWEX® MARATHON® MSC with different particle sizes at pH 6.0. Adsorption conditions were: 1 mg*mL-1 polyclonal IgG at 20 mM MES pH 6.0. The IgG concentration was measured at 280 nm in microtiter plates.

Figure 11A:
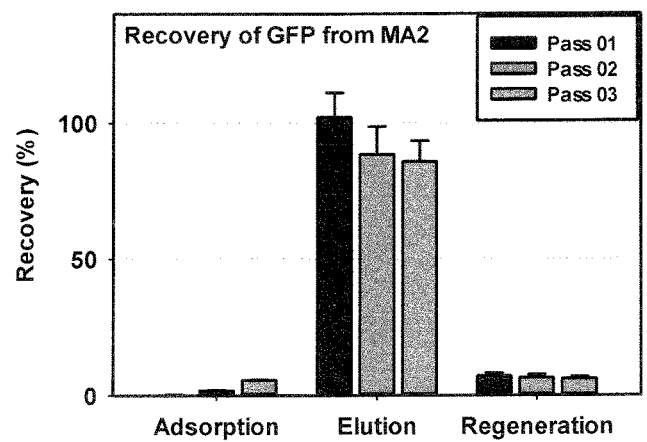
Figure 11B:
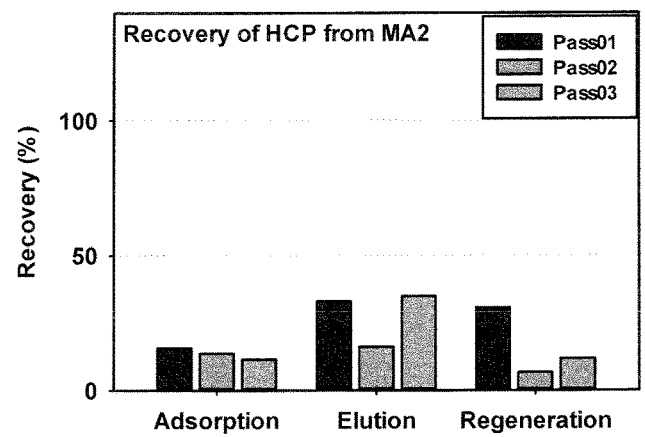
Figure 11C:
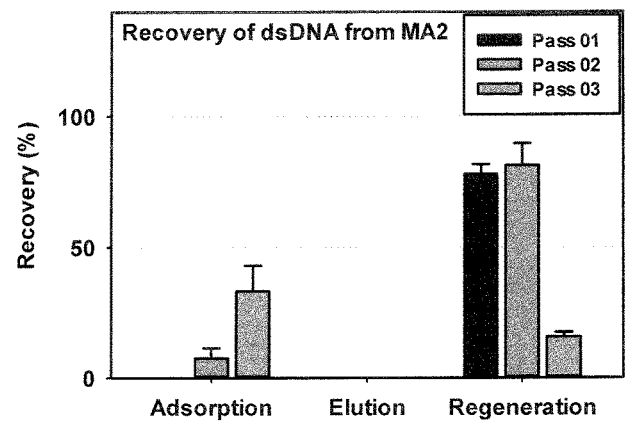

FIG. 11: Recovery (%) of GFP, HCP and dsDNA from ground DOWEX® MARATHON® A2 (MA2) after adsorption, elution and regeneration steps over pass 01, 02 and 03. Pass 01, 02 and 03 are used as synonyms for subsequently processing of the same sample. FIG. 11a-c shows the result for the recovery of GFP, HCP and dsDNA, respectively.

FIG. 12: Endotoxin concentration for the supernatants during the adsorption/elution experiment.

FIG. 13.1: Flocculated DOWEX® MARATHON® MSC with 10% DOWEX® MARATHON® A2 microparticles after about 30 seconds settling time.

FIG. 13.2: Boxplot of the calculated hydrodynamic diameter of formed flocs during the capture of pIgG on ground DOWEX® MARATHON® MSC with subsequent flocculation using ground DOWEX® MARATHON® A2. The hydrodynamic diameter $d_{10}$ is given as 10% percentile (90% of the flocs are larger than the given diameter). The data is grouped by the volumetric ratio of DOWEX® MARATHON® A2 (AIEX) to DOWEX® MARATHON® MSC (CIEX). Whiskers are plotted at 1.5 times the interquartile range. The red lines represent the median of the distribution. Blue plus signs are data points outside the range described by the whiskers.

FIG. 14.1: Velocity distribution for flocculated DOWEX® MARATHON® MSC microparticles.

FIG. 14.2: Flow chart describing the capture and elution of IgG from CHO cell supernatant.

FIG. 14.3: Cell capture using AIEX microparticles with subsequent capture of IgG. More than 99% of DNA and 60% of the host cell proteins are captured together with the cells.

FIG. 14.4: Recovery of IgG from DOWEX® MARATHON® MSC at different salt and buffer conditions. Polyclonal IgG at a concentration of 1 mg/mL was captured using ground DOWEX® MARATHON® MSC. Adsorption conditions were: 50 mM MES pH 6.0. Adsorption was conducted in 15 mL Falcon tubes for 15 minutes at 20 rpm on a rotary shaker. The resulting capacity of MARATHON® MSC was approximately 40 mg/mL. Microparticles were separated by centrifugation at 16000 rcf for 10 minutes. The volume of the assay was 2 mL. Elution was performed using 1 mL of corresponding buffer.

Figure 15:
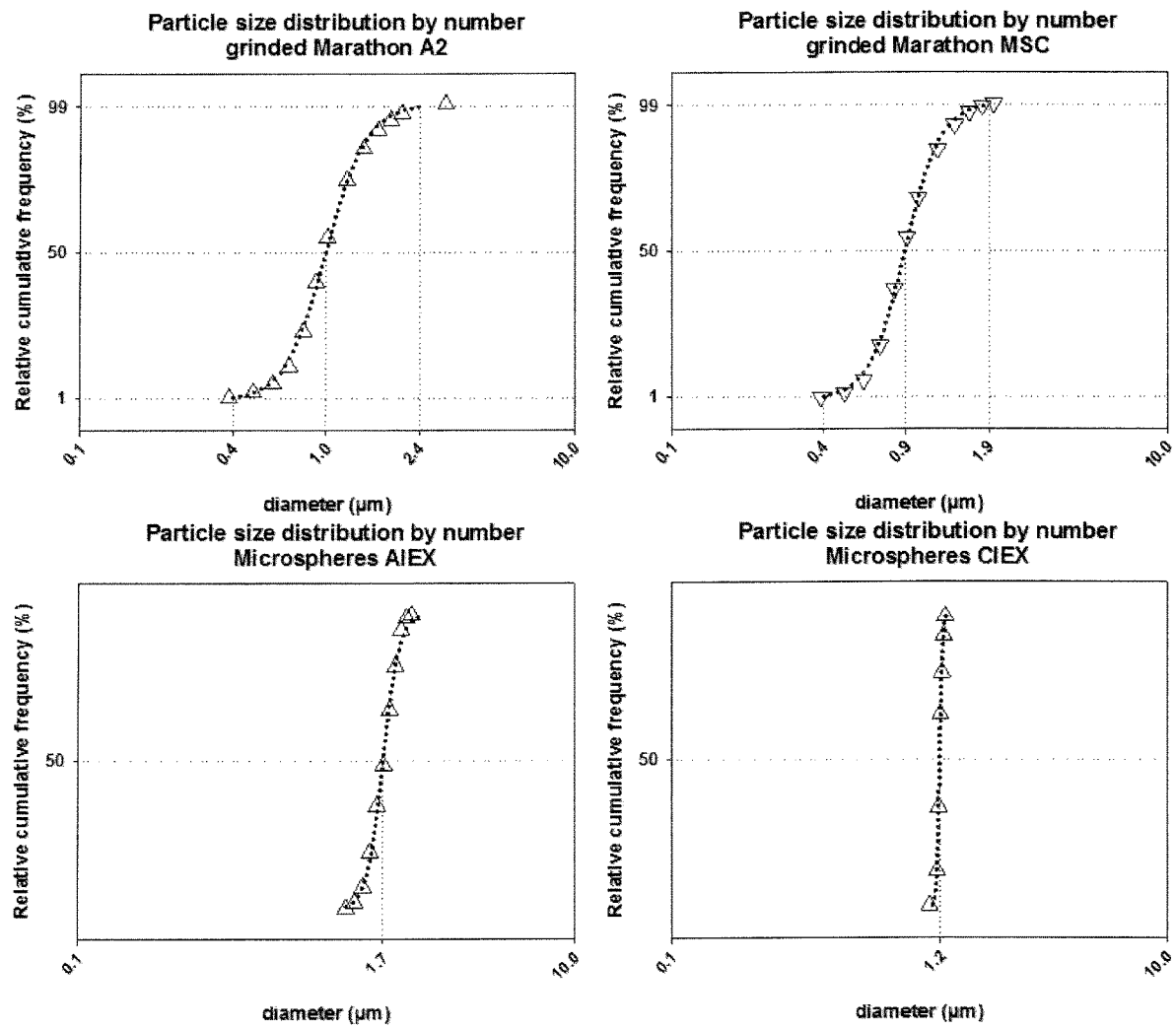

FIG. 15: Particle size distributions of ground microparticles DOWEX® MARATHON® A2 and DOWEX® MARATHON® MSC and commercially available microspheres AIEX and CIEX.

Figure 16:
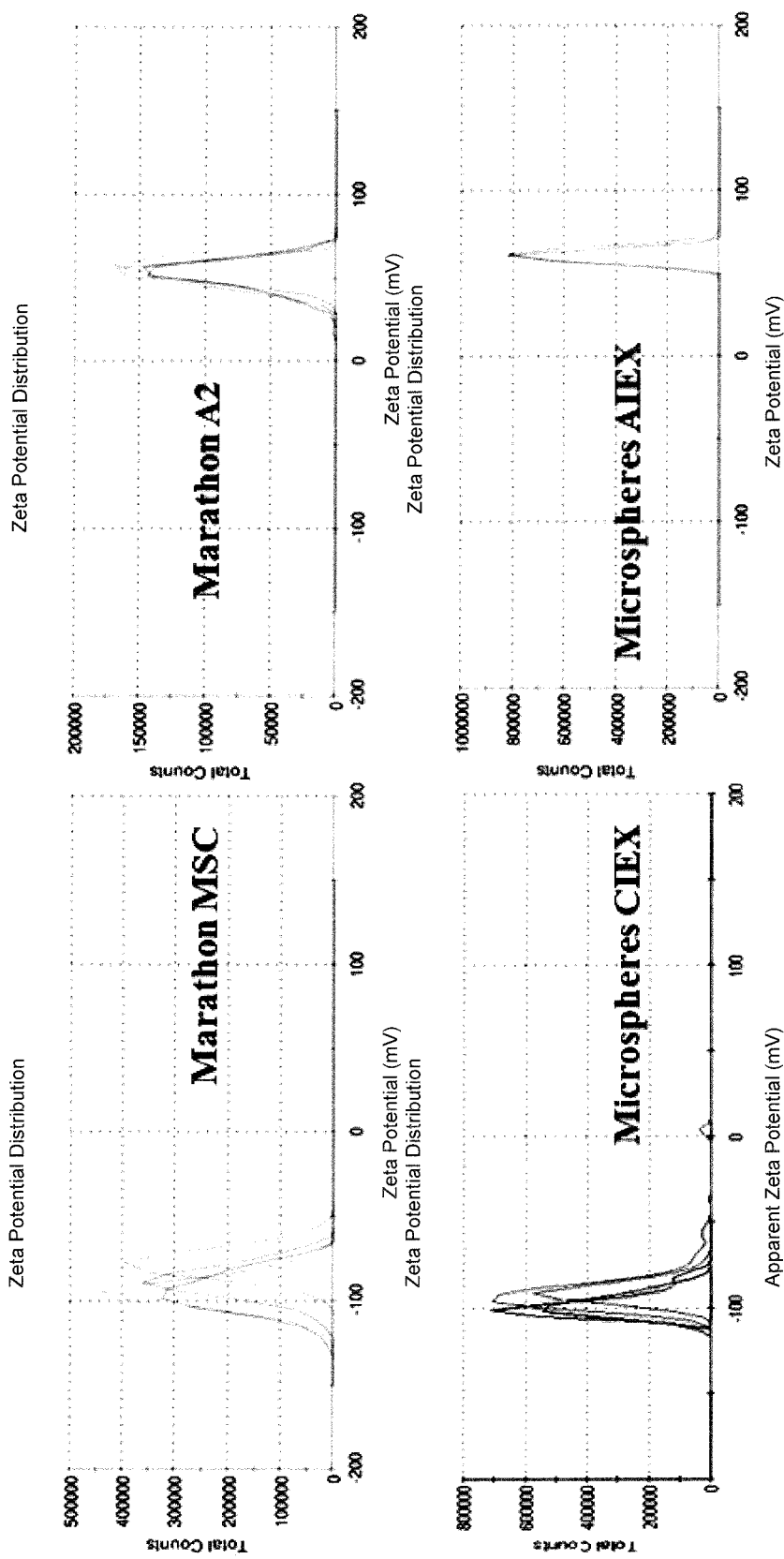

FIG. 16: Zeta potential of ground microparticles DOWEX® MARATHON® A2 and DOWEX® MARATHON® MSC and commercially available microspheres AIEX and CIEX.

Figure 17:
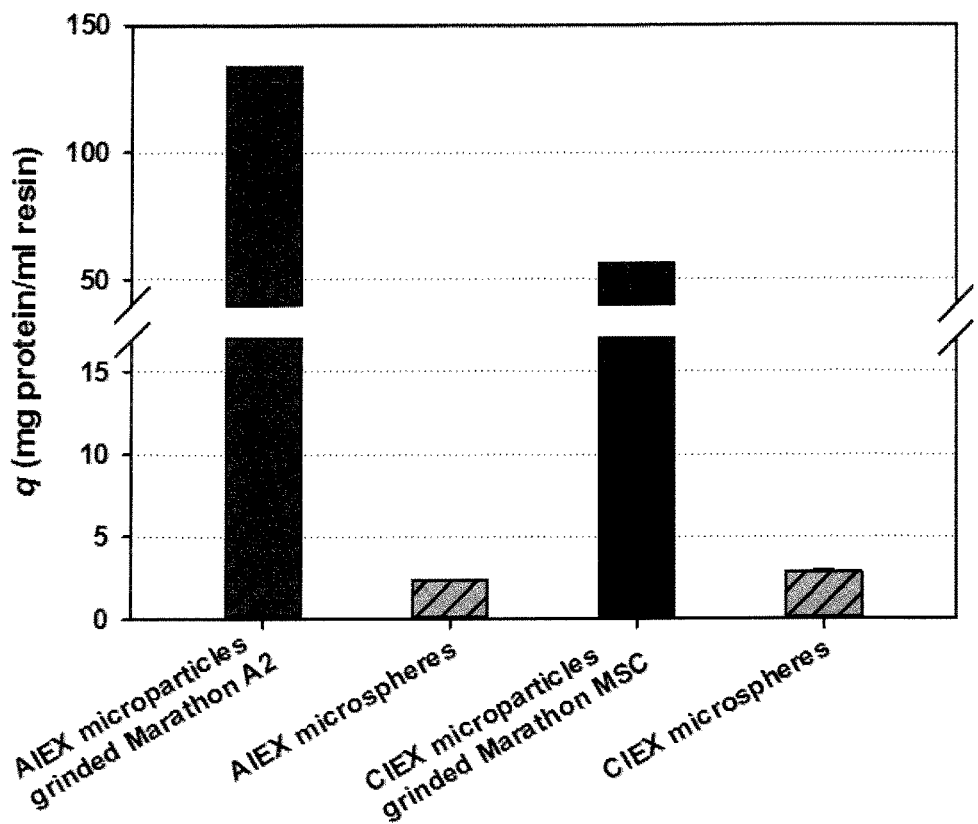

FIG. 17: Protein binding capacities of ground microparticles DOWEX® MARATHON® A2 and DOWEX® MARATHON® MSC and commercially available microspheres AIEX and CIEX.

Figure 18:
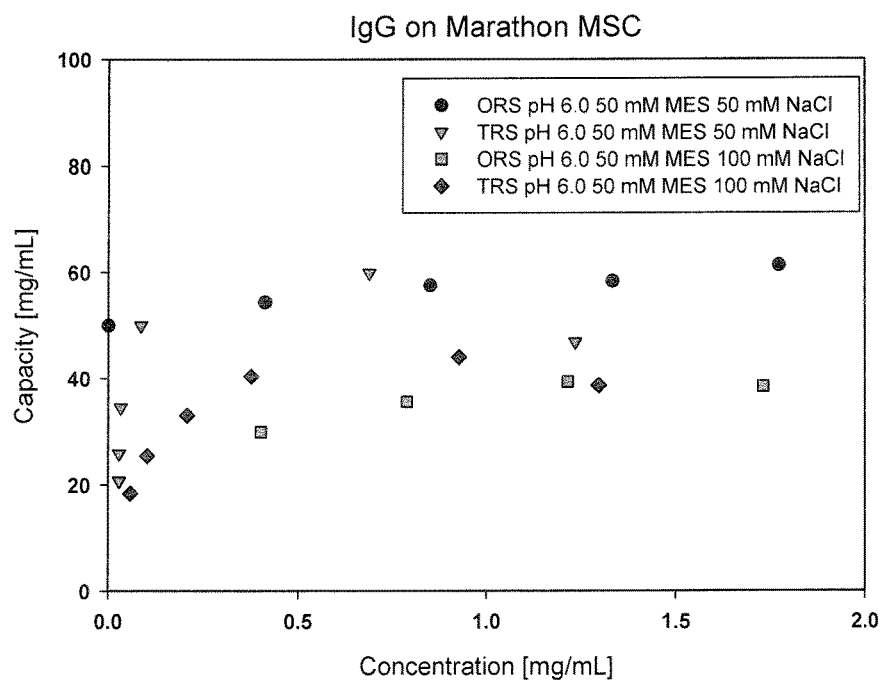

FIG. 18: Comparison of protein capacities for IgG on DOWEX® MARATHON® MSC (ORS) and preflocculated DOWEX® MARATHON® MSC (TRS). The ratio of DOWEX® MARATHON® A2 to DOWEX® MARATHON® MSC was 0.4. Adsorption was conducted for 15 minutes.

ITEMS OF THE INVENTION

The present invention can also be characterized by the following items:

1. A composition comprising positively charged microparticles and negatively charged microparticles, wherein the positively charged microparticles comprise ground polymeric anion-exchange resin, and wherein the negatively charged microparticles comprise ground polymeric cation exchange resin.
2. A composition comprising hydrophobic microparticles.
3. The composition of item 1, wherein the cation exchange resin is weakly or strongly acidic.
4. The composition of item 1, wherein the anion-exchange resin is weakly or strongly basic.

5. The composition of any one of the preceding items, wherein the anion-exchange resin and the cation exchange resin is polystyrene-based, Hydroxyethyl methacrylate (HEMA)-based, dimethylamino ethylmethacrylate (DMAEMA)-based, dimethylamino ethylmethacrylate (pDMAEMA), polyacrylamide based, methacrylic acid (MAA)-based.

6. The composition of any one of the preceding items, wherein the cation exchange resin and anion-exchange resin is polystyrene cross-linked with divinylbenzene-based.

7. The composition of any one of the preceding items, wherein the microparticles have an average particle size of less than about 5 µm.

8. The composition of any one of the preceding items, wherein the negatively charged microparticles can adsorb at least 5 mg of GFP using the conditions as set forth in example 4.

9. The composition of any one of the preceding items, wherein the positively charged microparticles can adsorb at least 5 mg of polyclonal IgG using the conditions as set forth in example 4.

10. The composition of any one of the preceding items, wherein said microparticles are obtainable by grinding anion-exchange resin and cation exchange resin and mixing said ground anion-exchange resin and said ground cation exchange resin.

11. The composition of any one of the preceding items, wherein the anion-exchange resin is AMBERLITE® IRA-485, AMBERLITE® IRA-400, DOWEX® 1X2-100, DOWEX® 1-8-100, DOWEX® MARATHON® A2 or DIAION® SA 20A.

12. The composition of any one of the preceding items, wherein the cation exchange resin is AMBERLITE® IRC-748, DOWEX® 50 WX2-100, DOWEX® 50 WX8-100, DOWEX® MARATHON® MSC or DIAION® SK 110.

13. The composition of any one of the preceding items, wherein the resin is non-porous.

14. The composition of any one of the preceding items, wherein the positively charged microparticles and/or negatively charged microparticles or hydrophobic microparticles is obtainable by grinding said resin and conditioning the resin.

15. The composition of any one of the preceding items, wherein said composition is in the form of a powder.

16. The composition of any one of the preceding items, wherein said composition is present in an liquid medium such as in a slurry or a suspension.

17. The composition of any one of the preceding items, wherein the ratio of positively charged microparticles and negatively charged microparticles is about 0.1:99.9 (w/w) to 99.9:0.1 (w/w).

18. Use of the positively charged microparticles and negatively charged microparticles or hydrophobic microparticles of any one of the preceding items to adsorb biomolecules, preferably a protein or a plasmid.

19. The use in item 17 to adsorb biomolecules, preferably proteins from cell homogenate or fermentation supernatant.

20. Use of the positively charged microparticles and negatively charged microparticles of any one of the preceding items to disrupt cells.

21. The use of the positively charged microparticles and negatively charged microparticles of items 1-16 to disrupt cells and to adsorb molecules, preferably biomolecules, more preferably polypeptides and polynucleotides.

22. A method of obtaining biomolecules from a biological fluid comprising said biomolecules comprising:
   a) adding the positively charged microparticles and adding the negatively charged microparticles of any one of items 1-16 to the biological fluid,
   b) allowing the microparticles to form flocs,
   c) removing the flocs from the biological fluid,
   d) desorbing the biomolecules from the flocs or purifying the biomolecules from the biological fluid in c).

23. The method according to item 21, wherein the biological fluid is cell homogenate or fermentation supernatant.

24. The method according to item 21, wherein the fluid is a cell suspension and wherein the method further comprises agitating the cell suspension after step a) and/or d).

25. The method according to items 21, 22 or 23, wherein step c) is carried out by separation, such as centrifugation or filtration.

26. The method according to any one of items 21 to 24 wherein in step a) the positively charged microparticles and negatively charged microparticles are added separately.

27. The method according to any one of items 21 to 24 wherein step a) comprises adding the negatively charged microparticles into the biological fluid, and then adding the positively charged microparticles into the biological fluid 28. A kit comprising the positively charged microparticles and negatively charged microparticles of any one of items 1-16 and optionally means for suspension.

29. A biological fluid comprising biomolecules and positively charged microparticles and negatively charged microparticles or hydrophobic microparticles as defined in any one of items 1-16.

30. The fluid of item 29 further comprising flocs.

31. Use of positively and negatively charged microparticles for biomolecule recovery, wherein the positively charged microparticles comprise ground polymeric anion-exchange resin, wherein the negatively charged microparticles comprise ground polymeric cation exchange resin, and wherein the biomolecule is acidic or basic.

32. Use of item 31 for biomolecule recovery from cell lysate or cell homogenate.

33. Use of item 31 for biomolecule recovery from cell suspension.

34. Use of positively and negatively charged microparticles for cell disruption and release of biomolecule from the cell, wherein the positively charged microparticles comprise ground polymeric anion-exchange resin, wherein the negatively charged microparticles comprise ground polymeric cation exchange resin, and wherein the biomolecule is acidic or basic.

35. A method of obtaining biomolecules from a biological fluid comprising a) adding positively charged microparticles and negatively charged microparticles to a biological fluid, and recovering the biomolecules from the biological fluid, wherein the biomolecule is acidic or basic.

36. The method of item 35 wherein the biological fluid is a cell suspension, cell lysate or cell homogenate.

37. A method of obtaining biomolecules from a cell, comprising a) adding positively charged microparticles or negatively charged microparticles to disrupt the cell, b) adding oppositely charged microparticles, and b) recovering the biomolecules.
38. The method of item 37, wherein the biomolecule is acid or basic.
39. The method of item 37, wherein positively charged microparticles is first added.
40. The method of item 55, wherein negatively charged microparticles is first added.

DETAILED DESCRIPTION OF THE INVENTION

The present invention provides simple and fast methods for recovering biomolecules using the adsorbent as described herein. The present invention is partly based on the surprising finding that the adsorbent comprising charged microparticles rapidly forms flocs of large diameters (such as at least 5 µm) which enables an easy separation of molecules, preferably biomolecules, from the biological fluid. Moreover, it has been found that the purification efficiency and impurity reduction of the present adsorbent is very high. As will be appreciated by a skilled person in the art, the present invention is particularly useful for separating proteins from cell homogenates and fermentation supernatants in large scale application, such as pilot or industrial scale as described herein. The adsorbent can be advantageously used in continuous process or batch process (referred to as batch adsorption).

The term "biomolecule" means a molecule that is normally found in or synthesized by an organism, including polypeptide or a polynucleotide. The biomolecules may be acidic or basic biomolecules. Examples of biomolecules include, but are not limited to, oligosaccharide, polysaccharide, lipopolysaccharide, oligopeptides, proteins, nucleosides, flavonoids, oligonucleotides, DNA (ds or ssDNA), plasmid DNA, cosmid DNA, BAC DNA, YAC DNA, RNA (ds or ssRNA), organometallic compounds, amino acids, lipids, pyrimidines, purines, carbohydrates, peptidomimetic compounds, toxins, steroids, enzymes. Said term also includes a "product" or "expression product" as described herein below. Biomolecules are preferably charged.

The adsorbent according to the present invention comprises ion exchange resin in the form of ground particles.

In the alternative, the adsorbent according to the present invention comprises hydrophobic resin in the form of ground particles. The outstanding protein adsorption capacities of such hydrophobic microparticles, which are superior to conventional chromatographic media at low salt concentration, are especially useful for e.g. negative purification of polynucleotides or hydrophilic proteins. Accordingly, the present invention provides uses and methods for negative purification of polynucleotides or hydrophilic protein by applying the hydrophobic microparticles. For that purpose To a homogenate or standard protein solution, 50% (v/v) hydrophobic microparticles suspensions are added to homogenate or protein solutions. Microparticles suspensions are incubated, e.g. for 30 minutes. Afterwards microparticles are centrifuged and elution of bound protein is performed by addition of elution buffer, mixing and incubation for e.g. 30 min. Optionally, a second washing step with elution buffer can be included. After elution microparticles are centrifuged again as before. Concentration of protein in supernatants can be quantified by e.g. photometric analysis and purity of target protein can be checked by SDS-PAGE.

In a first aspect, the present invention provides a composition comprising positively charged microparticles and negatively charged microparticles, wherein the positively charged microparticles comprise ground polymeric anion-exchange resin, and wherein the negatively charged microparticles comprise ground polymeric cation exchange resin.

A resin useful for the present invention is a solid, non-soluble polymeric material which is capable of interacting and attaching to various elements and allows for capturing of the elements from a mixture. Resins are generally composed of inert compound including, but not limited to, sephadex, polystyrene, polyacrylamide, polymethacrylate or neutral polysaccharides. They may also include cross-linked natural polymers like cellulose, dextran or agarose. Such resins become in accordance with the teaching of the present invention ground particles, i.e., microparticles.

As defined herein, "positively charged" microparticles have at least one elementary charge of a proton, and more typically more than one, at a neutral pH. "Negatively charged" microparticles have at least one elementary charge of an electron, and more typically more than one, at a neutral pH.

Microparticles according to preferred embodiments are prepared from ion-exchange resin, more preferably, polymeric anion-exchange resin and cation-exchange resin. Ion exchange resin refers to a solid support containing insoluble carrier of an electrical charge polymers carrying fixed functional groups or sites with exchangeable ions. Illustrative examples of suitable ion exchange resins include anion exchange resins, cation exchange resins, and mixed-mode chromatography resins, also sometimes called herein as mixed-mode ion exchange resins. The exchangeable ion form is generally one or more of $Na^+$, $H^+$, $OH^-$, or $Cl^-$ ions, depending on the type of ion exchangeable resin. Ion exchange resin includes weak and strong cation exchange resins and weak and strong base anion exchange resins. Ion exchange resins are widely used in various industrial fields. Ion exchange resins are commonly used, for example, in the field of water treatment such as demineralization of water for boilers or condensate treatment at power plants, in a food field such as purification for a sugar solution or in the field of super pure water for preparation of semiconductors.

Adsorbent particles in the present invention are preferably prepared from porous, spherical ion-exchange resins. Spherical ion-exchange resins are made by suspension polymerization, in which a monomer mixture comprising a monofunctional addition-polymerizable monomer and a radical polymerization initiator are added to a liquid medium, followed by stirring to prepare a suspension of the monomer mixture. The suspension is then maintained at a polymerization temperature for a period of time to obtain a spherical cross-linked copolymer. The diameter of ion-exchange resins for water treatment is typically between 300-600 µm.

Polymer matrices of ion exchange resins may include polystyrene, polystyrene and styrene copolymers, polyacrylate, aromatic substituted vinyl copolymers, polymethacrylate, phenol-formaldehyde, polyalkylamine, combinations thereof, and the like. In a preferred embodiment, the polymer matrix is polystyrene and styrene copolymers, polyacrylate, or polymethacrylate, while in another embodiment, the polymer matrix is styrenedivinylbenzene copolymers. Preferably, the ion-exchange resin for the preparation of adsorbent particle uses resin which are polystyrene-based, Hydroxyethyl methacrylate (HEMA)-based, dimethylamino ethyl methacrylate (DMAEMA)-based, dimethylamino ethyl methacrylate (pDMAEMA), methacrylic acid (MAA)-based. Most preferably, the resin is made from polystyrene cross-linked with divinylbenzene.

The cation exchange resin used herein can be weakly or strongly acidic. As used herein, the term "weakly acidic cation exchange resin" refers to a resin having an apparent dissociation constant or ionization constant (pKa) greater than about 4.5 as measured by conventional methods (for example, Fishery et al., J. Phys. Chem., 60, 1030 (1956)). It may have the carboxylic acid group, a phenolic hydroxyl group, a phosphonic acid group, and an arsono group as the exchange group. Typically, such resins are those of the polyacrylic acid type or the polymethacrylic acid type. Preferably, the resin has the methacrylic acid type.

The adsorption strength of various ions on the weakly acidic cation exchange resin is generally analogous to that on the strongly acidic resin. Selectivity is higher for higher valence ions.

The term "strongly acidic cation exchange resin," on the other hand, refers to a resin having a pKa less than about 1.5. A strongly acidic cation exchange resin may have sulfonic acid groups such as sodium polystyrene sulfonate or polyAMPS. The sulfonic acid group (—HSO3) is the exchange group and behaves like a strong acid, dissociating to (—SO3)- and H+ even in acidic solutions, not to mention in alkaline solutions.

The anion-exchange resin used herein can be weakly or strongly basic. As used herein, the term "weakly basic cation exchange resin" refers to a resin having an apparent dissociation constant or ionization constant (pKa) greater than about 8.5 as measured by conventional methods (for example, Fishery et al., J. Phys. Chem., 60, 1030 (1956)). It may have the primary, secondary, and/or ternary amino groups, e.g. polyethylene amine as the exchange group. The term "strongly basic anion exchange resin," on the other hand, refers to a resin having a pKa less than about 12. A strongly basic anion exchange resin may have quaternary amino groups, for example, trimethylammonium groups, e.g. polyAPTAC, as the exchange group.

The skilled person is able to select the anion exchange resin or cation exchange resin used for the adsorption of biomolecules. There are several parameters which determine the adsorption capacity of biomolecules and the ion exchanger. It is within the general knowledge of the skilled person to determine which biomolecules can be adsorbed by which type of ion exchangers under what conditions. The choice of the adsorbent depends in particular on the isoelectric point (IEP) of the biomolecule of interest and/or on its overall hydrophilic nature. The pH of the biomolecule solution and the isoelectric point (IEP) of the biomolecule such as protein largely determine whether it will bind to the cation or anion ion exchanger. It is known that proteins bind to a cation ion exchanger at a pH below the IEP of the biomolecule or an anion exchanger at a pH of above the IEP.

Commercially available ion exchange resins are for example provided by Rohm & Haas of Philadelphia, Pa. USA as AMBERLITE®, Amberjet, Duolite, and Imac resins, from Bayer of Leverkusen, Germany as Lewatit resin, from Dow Chemical of Midland, Mich. USA as Dow resin, from Mitsubishi Chemical of Tokyo, Japan as DIAION® and Relite resins, from Purolite of Bala Cynwyd, Pa. USA as Purolite resin, from Sybron of Birmingham, N.J. USA as Ionac resin, and from Resintech of West Berlin, N.J. USA.

Positively charged microparticles can be prepared from polymeric anion exchange resin. Commercially available anion exchange resins are typically in either OH− or Cl− forms. In one embodiment, the anion exchange resin is in the OH− form. The resin may be for example "DIAION®" anion exchange resins such as DIAION® SA resins (including DIAION® SA 20A) and DIAION® SK resins (including DIAION® SK 110) (from Mitsubishi Chemical) "AMBERLITE®" resins such as AMBERLITE® IRA-400, AMBERLITE® IRA-734, and AMBERLITE® IRA-900 (from Rohm & Haas Co.) or "DOWEX®" resins such as DOWEX® 1, DOWEX® 2, DOWEX® 11, DOWEX® 21K, DOWEX® 1×2, DOWEX® 1×4, DOWEX® 1×8 and DOWEX® MARATHON® resins (from Dow Chemical Co). Preferably, fine mesh spherical ion exchange resins DOWEX® 1×2, DOWEX®1×4, 1×8 are used. Functional groups in anion exchange resins may include quaternary ammonium groups, e.g., benzyltrimethylammonium groups (type 1 resins), benzyldimethylethanolammonium groups (type 2 resins), trialkylbenzyl ammonium groups (type 1 resins), dimethylethanolaimne (type 2) or tertiary amine functional groups.

Negatively charged microparticles can be prepared from polymeric cation exchange resin. Commercially available cation exchange resins are typically in either H+ or Na+ forms. In one embodiment, a cation exchange resin is in the H+ form. The resin may be for example "DIAION®" cation exchange resins such as DIAION® PK resins and DIAION® SK resins (from Mitsubishi Chemical) or "DOWEX®" resins such as DOWEX® 50WX2, DOWEX® 50WX8, and DOWEX® MARATHON® resins such as MARATHON® C, DOWEX® MARATHON® MSC (from Dow Chemical Co). Functional groups of a cation exchange resin may include sulfonic acid groups (—SO₃H), phosphonic acid groups (—PO₃H), phosphinic acid groups (—PO₂H), carboxylic acid groups (—COOH or —C(CH₃)—COOH), combinations thereof. In one embodiment, the functional groups in a cation exchange resin will be —SO₃H, —PO₃H, or —COOH, while in the most preferred embodiment; the functional groups in a cation exchange resin is —SO₃H.

As used herein, a polymeric material may refer to a polymer, a mixture of polymers, a cross-linked polymer, mixtures thereof, or to polymeric networks. Often, a polymeric material is simply referred to as a polymer.

Polymeric cation exchange resin, as used herein, refers to a polymeric material having one or more elementary charges of the proton, or to such a macromolecule itself. A polymeric anion exchange resin has one or more elementary charges of the electron.

The positively charged microparticles of the invention are particles having at least one elementary charge of a proton, and more typically more than one, at a relatively neutral pH, whereas the negatively charged microparticles have at least one elementary charge of an electron at these conditions.

Positively or negatively charged microparticles are obtained when at least a fraction of the constituents of the microparticles are ionically charged.

The ratio between positively charged microparticles and negatively charged microparticles can be from about 0.1:99.9 (w/w) to 99.9:0.1 (w/w). For example, it can be about 50:50, but it can also be different, such as 90:10, 80:20, 75:25, 60:40, 40:60, 20:80, 25:75, 10:90, etc. Preferred ratio is about 90:10.

Hydrophobic microparticles of the present invention are preferably grinded overnight Grinded resins are suspended in water. Supernatant is centrifuged. Resins are re-suspended in salt solution, such as 2 M sodium chloride and centrifuged, a pellet is discarded. Supernatant are transferred and centrifuged again. Supernatant is discarded. Ground resins are re-suspended in water and transferred to tubes. Resins are centrifuged, supernatant is discarded and resin is resuspended in aqueous washing solution. Wash sequence is:

1×50% EtOH (dilution of organic residues)
3× deionized water (dilution of EtOH)

In one preferred embodiment, the microparticles are in the form of ground particles having an average particle size less than about 10 µm, such as less than about 9 µm, 8 µm, 7 µm, 6 µm, 5 µm, 4 µm, 3 µm, 2 µm, and 1 µm. Preferably, the ground particles have an average particle size less than about 5 µm, and more preferably less than 2.5 µm. Preferably, the ground particles have an average particle size larger than 0.5 µm. Accordingly, the ground particles may preferably have an average particle size in the range from about 10 µm to 0.5 µm, about 9 µm to about 0.5 µm, about 8 µm to about 0.5 µm, about 7 µm to about 0.5 µm, about 6 µm to about 0.5 µm, about 5 µm to about 0.5 µm, about 4 µm to about 0.5 µm, about 3 µm to about 0.5 µm, or about 2.5 µm to about 0.5 µm. However, the ground particles may have a particle size more than 10 µm as well as less than 0.5 µm.

Preparation of Adsorbent Particles

Microparticles are obtainable by grinding anion-exchange resin and/or cation exchange resin. Preferably, the microparticles of the present invention are obtainable by (or are obtained by) grinding the resin and conditioning the resin.

It is preferable to condition the ground particles to remove residual by-products in the manufacturing process of the resin. Typical conditioning methods for ion exchange resins are well known in the art and also described by the suppliers.

If necessary, "conditioning" can be performed in order to transfer the resin from the $H^+$ or $OH^-$ to $Na^+$ or $CI^-$ form. In one embodiment, conditioning is performed by repeated washing steps using NaCl and water. In the process, the resin can be ground in water and sedimentation can be done by centrifugation, which has the advantage of removing very small microparticles. Very small particles are microparticles that do usually not sediment but float at the surface. As such they may be decanted or mechanically removed. Alternatively, resins already in $Na^+$ or $Cl^-$ form are also available commercially and can be obtained from the suppliers.

In a preferred embodiment the microparticles are prepared by (a) grinding the ion exchange resin, (b) resuspending said ground resin in water, (c) allowing sedimentation of said ground resin, (d) collecting ground resin from the supernatant of the sedimented suspension, (e) resuspending collected ground resin in about 2 M sodium chloride, (f) allowing sedimentation of said ground resin, (g) collecting ground resin from the supernatant of the sedimented suspension of (f), (h) allowing sedimentation of said ground resin, (i) collecting the sediment of the ground resin of (h), and (j) washing said collected ground resin.

Grinding

Grinding can be carried out in any way known in the art, including, but not limited to, by a grinding device, such as a grinding mill (including a jet mill, a ball mill, a hammer mill or the like), or by hand with for example a mortar and pestle. "Grinding" as used herein refers to an operation leading to a reduction in the particle size. A skilled person can readily select grinding methods to prepare the resins. In one embodiment, the resin is wet ground in an automated manner by moving one or more pestles in a mortar. The grinding process may be continued until the majority of the particles have a size of less than about 10 µm, such as less than 9, 8, 7, 6, 5, 4, 3, 2, 1 are obtained. Preferably, resin is ground such that the majority of the particles have an average particle size as described below. By majority it is meant more than 50%, such as more than 60%, 70%, 80%, 90%, or 95%. In other embodiments, the majority of the particles have an average particle size of at least 0.1 µm, such as 0.2 µm, 0.3 µm, 0.4 µm, 0.5 µm, 0.6 µm, 0.7 µm, 0.8 µm, 0.9 µm, 1.0 µm, 1.1 µm, 1.2 µm, 1.3 µm, 1.4 µm 1.5 µm, 1.6 µm, 1.7 µm, 1.8 µm, 1.9 µm, 2.0 µm, 3 µm, 4 µm and 5 µm.

A skilled person can readily determine the size of ground particles with methods known in the art. From that, the average particle size can be determined by means and methods known in the art. For example, the size can be determined by optical microscopy using a software-based determination of size such as illustrated in the example. Particle size of ground resin can be determined at 1000-fold magnification by estimation of equivalent circular diameters. Distribution is preferably calculated by comparison of diameter sizes of about 100-500 particles at 1% v/v. Grinding breaks up the narrow pores and has the effect of increasing surface area, which leads to a significant increase in the binding capacity of biomolecules, particularly for proteins or polypeptides as well as a very rapid binding kinetic. Determination of the diameter is preferably done with the aid of technical means such as a software which recognizes a particle and measures the diameter.

"Resuspending" or "suspending" or any grammatical form thereof when used herein means that microparticles are brought into suspension.

"Allowing sedimentation" when used herein means that microparticles are allowed to settle out of the fluid in which they are entrained and come to rest against a barrier. The sedimentation is due to the particles motion through the fluid in response to forces acting on them. These forces can be gravity or centrifugal acceleration by, e.g., a centrifuge, with the latter being preferred.

"Collecting" means that microparticles are harvested from the suspension.

"Washing" when used herein means that residual amounts of fluids that could disturb or interfere with the performance of the microparticles are reduced. Preferably, the washing step has the following sequence: 1×50% ethanol, 3× water, preferably deionized, 1×0.5M NaOH, 4× water, preferably deionized water and resuspending in water, preferably deionized water. The volume of each of these fluids is in excess of the volume of microparticles, preferably 10- or 20-fold in excess.

After the grinding process, particles outside the preferred range can be optionally removed, for example, by centrifugation, sedimentation, filtration, or any other methods known to a skilled person in the art.

The negatively charged microparticles can adsorb at least 5 mg, such as at least 6, 7, 8, 9, 10, 15, 20, 25, 30, 35, 40, 45, 50, 55, 60, 65, 70, 75, 80, 85, 90, 95, 100, of GFP using the condition as set forth in example 4. The positively charged microparticles can adsorb at least 5 mg, such as at least 6, 7, 8, 9, 10, 15, 20, 25, 30, 35, 40, 45, 50, 55, 60, 65, 70, 75, 80, 85, 90, 95, 100, of polyclonal IgG using the condition as set forth in example 4.

Surprisingly, it has been found that the rough surface in the ground particles provides a comparable specific area for adsorption compared to macro-porous media having high binding capacity such as the Nuvia media developed by Bio-Rad Laboratories (USA). Nuvia media include Nuvia S Media—online Catalog 2013, No. 156-0311, Nuvia Q Media—online Calalog 2013, No. 156-0411, or Nuvia cPrime media—online Catalog 2013 No. 156-3401) developed by Bio-Rad Laboratories (USA).

Composition

The presently claimed composition may be prepared by mixing positively-charged microparticles with negatively-charged microparticles in the form of powder or in a suspension. It is also possible to prepare the positively-charged microparticles and negatively-charged microparticles in separate suspensions and then mixing the suspensions.

Method of Adsorbing Biomolecules

The present invention in further aspects involves the use of positively charged microparticles and negatively charged microparticles to obtain biomolecules from a fluid. As used herein, a "fluid" refers to an amorphous substance that tends to flow.

In accordance with one aspect of the invention, a method of obtaining a molecule, preferably a biomolecule, in particular a polypeptide, from a biological fluid is provided. The method comprises:
 a) adding the positively charged microparticles and negatively charged microparticles into the biological fluid,
 b) allow the particles to form flocs,
 c) removing the flocs from the biological fluid,
 d) desorbing the biomolecules from the flocs or purifying the biomolecules from the biological fluid in c).

In another embodiment, the positively charged microparticles and negatively charged microparticles are employed such that they are added into the biological fluid separately. The present thus encompass the following method:
 a) adding the either positively charged microparticles or negatively charged microparticles into the biological fluid,
 b) adding the oppositely charged microparticles into the biological fluid,
 c) allowing the particles to form flocs,
 d) removing the flocs from the biological fluid,
 e) desorbing the biomolecules from the flocs or purifying the biomolecules from the biological fluid in c).

Addition of Microparticles

In the first step, the microparticles are added into the fluid. The presently disclosed adsorbent can be used in laboratory scale, pilot-scale or industrial scale. As used herein, "lab-scale" comprises batch adsorption of a biomolecule from about 1 or 10 ml fluid to about 1000 ml fluid (1 liter *E. coli* cell homogenate or fermentation supernatant usually corresponds to about 450-550 g *E. coli* wet cell weight). As used herein, "pilot-scale" comprises batch adsorption of a biomolecule from about 1 liter fluid to about 10 liter fluid (10 liter *E. coli* cell homogenate or fermentation supernatant usually corresponds to about 4.5-5.5 kg *E. coli* wet cell weight). As used herein, "industrial scale" or large-scale comprises batch adsorption of a biomolecule from about 10 liter fluid to about 1000 or even 10000 liter fluid (10000 liter *E. coli* cell homogenate or fermentation supernatant usually corresponds to about 4.5-5.5 tons *E. coli* wet cell weight or even more).

The microparticles can be added into the biological fluid from which biomolecules are to be separated. The term "biological fluids" should be understood broadly. They refer to any fluid associated with organisms, such as obtained from or produced by any organisms. Examples of biological fluids include cell culture media, fermentation supernatants, fermentation broths, cell suspensions, cell lysate. Further examples of biological fluids are described herein above. In other embodiments, biological fluids may also be saliva, urine, lymphatic fluid, prostatic fluid, seminal fluid, blood, plasma, sera, sweat, mucous secretion, milk, milk whey, ascites fluid, organ extracts, plant extracts, animal extract. In a preferred embodiment, the biological fluid is any biological fluid described herein, such as a polypeptide or polynucleotide, e.g., plasmid DNA, cosmid DNA, BAC DNA, minicircle DNA, etc. containing fluid, derived from various in vitro or in vivo processes, and particularly, fermentation broth, culture broth, fermentation supernatant, culture supernatant, cell homogenate, cell lysate, or cell suspension. "Cell homogenate" is generally understood as a mixture of broken cells. Cell homogenate may be obtained by a mechanical or chemical method. For example, cells can be homogenized by conventional methods such as high pressure in a homogenizer to render a fermentation homogenate, or by simply vortexing in a lysis solution, including alkaline lysis.

Therefore, the present invention also includes a fluid comprising biomolecules and positively and negatively charged microparticles or hydrophobic microparticles. In preferred embodiments, the biological fluid is agitated during and/or after any of the steps of the methods of the present invention, but preferably not during the step when the particles are allowed to form flocs and/or when the flocs are removed from the biological fluid.

During and/or after the microparticles are added into the biological fluid they can be mixed by stirring or shaking to obtain a homogenous mixture. Without being bound by theory, it is assumed that adsorption takes place spontaneously while the particles are mixed with the biological fluid.

In a preferred embodiment, the microparticles are added first into the biological fluid to disrupt the cells. In fact, it has been surprisingly found that the microparticles of the present invention can be used to disrupt cells and adsorb the biomolecules within the cell thus rendering, for example, the use of high pressure homogenization unnecessary. Another use of positively charged microparticles and negatively charged microparticles is for the disruption of cells as well as the (combined) use thereof for the disruption of cells and the adsorption of molecules, preferably biomolecules, preferably a protein or a polynucleotide as described herein.

Flocculation

The next step is to allow the formation of flocs. It has been surprising found that the adsorbent particles will adsorb the biomolecules and rapidly form flocs of large diameter with the biomolecules. Flocs will form upon adsorption of the biomolecule (when the positively and negative charged microparticles are first mixed and then added to the biological fluid) and as well as upon addition of the oppositely charged microparticles after the addition if the microparticles are added separately.

In one embodiment the oppositely charged microparticles are added at different times. When the biomolecule is acidic, positively charged microparticles can be added to a biological fluid such as a cell lysate or cell homogenate for adsorption. Positively charged microparticles may also be added to a cell suspension, either at an amount only sufficient to disrupt the cell and to release the biomolecule, or at an higher amount which will disrupt the cell as well as adsorb the biomolecules. A skilled person is able to determine the amount necessary to partially or fully disrupt the cell. Negatively charged microparticles may be added thereafter, which works as cross-linker to increase the particle size and stability of the flocs. Alternatively, negatively charged microparticles such as prepared from chelating cation exchange resin may also be added to first to the cell suspension at an amount sufficient to disrupt the cell and to release the biomolecule. Then positively charged microparticles may be added to increase flocculation.

The biomolecule to be recovered can in some instances be basic. In this case, positively charged microparticles may be first added to a biological fluid such as a cell lysate or cell homogenate to form flocs with the cell debris or other impurities such as DNA, host cell proteins and cell fragments. Then, negatively charged microparticles may be added to increase flocculation, so the flocs can be easily separated and discarded. The basic biomolecules can then be recovered from the supernatant. Alternatively, use of either positively or negatively charged microparticles may be added to a cell suspension for cell disruption, which will result in the release of biomolecules in the supernatant. The supernatant can be further processed for purification.

The flocs typically have a size of 100 μm or even larger which makes it visible. This formation facilitates the separation of flocs including the biomolecules adsorbed thereon by gravity or filtration. This means that other unwanted material such as cell debris can be easily removed by filtration rendering centrifugation unnecessary. The present invention is therefore faster and simpler than prior art methods. Furthermore, it is not necessary to regenerate the resin that is required by column chromatography. The microparticles are cheaper material can be discarded after use.

Furthermore, after the biomolecules are desorbed by a desorption buffer, it is easy to separate the flocs formed from the desorption buffer due to its size.

In preferred embodiments, flocs have an average particle size of at least 5 μm, such as at least 10, 20, 30, 40, 50, 60, 70, 80, 90, 100, 200, 300, 400, 500, 600, 700, 800, 900, 1000 μm or more are formed.

The inventors have observed that flocculation with only positively charged or negatively charged microparticle becomes problematic after desorption of biomolecules. After desorption, the microparticles will form a homogenous suspension where the biomolecules cannot be easily separated therefrom. Hence, a centrifuge or a microfilter would be required to separate the biomolecules from the particles. However, it has been surprisingly discovered that when an oppositely charged microparticle additionally used, the microparticles remain as flocs even after desorption, and can be easily separated from the biomolecule by simple sedimentation, even in the case for smaller particles. Therefore, the inventors have found that a combination of both positively charged microparticles and negatively charged microparticles has the unexpected advantage which allows the use of microparticles with smaller diameters. This is advantageous since the use of microparticles with smaller diameters (such as smaller than 1 μm) allows a higher amount of biomolecules per volume to be processed. Furthermore, the present invention allows the use of simple mixer-settler equipment which offers a simple operation procedure.

Removal of Flocs

Generally, removal of the flocs from a liquid (such as a biological fluid or a buffer) can be performed by filtration, centrifugation, sedimentation, or any other suitable means. A skilled person can readily determine what methods can be used to separate or desorb the flocs from the fluid. The suspension of the flocs can for instance be processed in either a bucket centrifuge (laboratory scale), tubular centrifuge, decanter or disk stack centrifuge for pilot and industrial scale operation. Likewise, it is possible to remove the flocs by filtration where the flocs are retained, or by sedimentation or extraction. Desorption can be achieved by extraction decanter, mixer-settler or column extractor. Other useful methods for removal may be tangential flow filtration, deep-bed filtration, Dead End Filtration, or methods involving the use of filter press, nutsche filter.

Desorption of Biomolecules

Desorption can be carried out using any methods known in the art. For example, desorption can be carried out by resuspending the flocs in a buffer which allow the desorption of biomolecule such as proteins (desorption buffer). This can be achieved by using any known means in the art, including a tubular (static) mixer or other mixing devices such as stirred tank. Desorption can also be achieved by extraction decanter, mixer-settler or column extractor.

The suspension is then subject to conditions suitable for desorption. A skilled person can readily determine such conditions for desorbing the biomolecules adsorbed on the flocs. Generally, desorption methods used in conventional ion-exchange chromatography can be employed. For instance, desorption can be carried out by elution at a pH below or above the isoelectric point or by increased salt concentration.

The biomolecules can be further purified or enriched by methods known in the art. These include, for example, precipitation, crystallization and/or chromatography selected from the group consisting of hydrophobic interaction chromatography, affinity chromatography, pseudo-affinity chromatography, anion or cation exchange chromatography and/or size exclusion chromatography. Accordingly, the methods described herein include in a preferred embodiment a further step of purifying and/or enriching the (desired) biomolecule, in particular a protein, by making use of precipitation and/or chromatography as described before.

Finally, the biomolecule that was adsorbed by the adsorbent of the invention is recovered. "Recovering the biomolecule" in all its grammatical forms includes that a biomolecule is obtained, harvested, achieved, received or gained, which may be plasmids, polynucleotides or expression products such as peptide, proteins, including proteins that are glycosylated or post-transnationally modified. The biomolecule may be isolated and/or further processed, for example, it may be purified, for example, by means and methods known in the art and/or described elsewhere herein. Moreover, the termrecovering the biomolecule also includes that host cells are disrupted to release the product, preferably to such an extent that adsorption by the adsorbent of the invention is possible, and that further purification and/or enrichment of the product becomes feasible.

The methods of the present invention may also include a step of recovering the flocs from the desorption buffer.

In one embodiment, the method can be carried out with the following steps:

obtaining and optionally preparing the biological liquid by for example adjusting the concentration or pH, salinity, or diluting the biological liquid, adding the positively charged microparticles and negatively charged microparticles into the biological fluid at the same time or separately, shaking or stirring, allow the biomolecule of interest to adsorb/bind, allow the particles to form flocs, removing the flocs from the biological fluid for example by settling, centrifugation or filtration, wash the removed flocs to separate residual impurities of the liquid, adding appropriate desorption buffer, shaking or stirring, allowing biomolecule of interest to desorb from the microparticles, removing the flocs from the desorption buffer for example by settling, centrifugation, or filtration, washing the flocs to obtain the residual biomolecule from the flocs, desorbing the biomolecule from the flocs.

Cultivating Cells which Produce Biomolecules (the "Product")

Prior to applying the adsorbent of the invention, the method of obtaining a biomolecule as defined and described herein may optionally comprise the step of cultivating a (host) cell that produces, such as expresses, a biomolecule (the "product"), preferably an expression product such as a protein or polynucleotide. The term "cultivation of cells" or "culturing of cells" in medium (either with serum or serum free) in the context of the host cells of the present invention refers to the seeding of the cells into the culture vessel, to the growing of the cells in medium until, in case of adherent culturing, a monolayer is formed, or, in case of a suspension culture, a sufficient cell density is established and/or to the maintenance of the cells in medium as soon as the monolayer is formed or to the maintenance of the cells in suspension, respectively. The term "cultivation of cells" or "culturing of cells" in medium also includes that all of the above mentioned steps are performed with serum free medium, so that no or essentially no animal serum products are present during the whole cultivation process of the cells. Cells may be cultivated by exponential feed, or linear or constant feed or other type of feed, fed batch cultivation, or high density cultivation. Yet, in the alternative, the above mentioned steps may also be performed with serum containing medium.

The nucleotide sequence and/or the encoded polypeptide may or may not be heterologous with respect to the cell. By "heterologous," this means derived from a cell or organism with a different genomic background, or is homologous with respect to the (host) cell, but located in a different genomic environment than the naturally occurring counterpart of said nucleotide sequence. This means that, if the nucleotide sequence is homologous with respect to the host, it is not located in its natural location in the genome of said host, in particular it is surrounded by different genes.

A "cell" when used herein refers to a cell which is capable of producing a biomolecule. Said cell is applied in the methods and uses of the present invention. For that purpose, if the cell is to express a polynucleotide or a polypeptide, a nucleotide sequence for producing the polynucleotide or polypeptide is introduced in the cell.

The cell from which biomolecules are recovered can be either, prokaryotic cells, eukaryotic cells, or both. More preferably, the cell applied in the methods of the present invention are vertebrate cells including mammalian, avian, amphibian and fish cells and insect cells. Also included by the term cells are eukaryotic cells. Typically, eukaryotic cells are human cell lines, mammalian cells, avian cells or insect cells. A cell also includes yeast cell or fungal cells. However, it is preferred that the cell is a prokaryotic cell including bacterial cells from gam-negative bacteria such as cells from Enterobacteriaceae, e.g. *E. coli* or Pseudomonadaceae, e.g., *P. putida, P. Fluorescens* or gram-positive bacteria such as cells from Lactobacteriaceae or Bacillaceae. Most preferably however, the cell is *E. coli*.

In a preferred embodiment of the present invention, the expression product is a proteinaceous product. "Proteinaceous" when used herein refers to any of a group of complex organic macromolecules that contain carbon, hydrogen, oxygen, nitrogen, and usually sulphur and are composed of one or more chains of amino acids. A preferred proteinaceous expression product is a polypeptide (of interest). Accordingly, the term "proteinaceous" also means relating to, consisting of, resembling, or pertaining to protein. In a more preferred embodiment of the present invention, the product may be a polypeptide of interest which is expressed and thus produced. It is preferred that the product is biologically active. The proteinaceous product may be acidic or basic.

The expression product can be the product of transcription and/or translation of a nucleotide sequence, preferably of a nucleotide sequence that is exogenously added to the cell by means and methods commonly known in the art in the context of genetically engineering host cells. The product can be a nucleotide sequence including, for example, a plasmid, mini-circle DNA, cosmid, BAC, a ssDNA or dsDNA sequence or RNA sequence (ribozyme, antisense RNA, sRNA, iRNA, miRNA and the like), all of which are capable of being produced in the host cell or it can be a polypeptide that is generated by way of translation of the transcribed RNA in the cell.

A "polypeptide" includes proteins, polypeptides and fragments thereof, said fragments being preferably biologically active. The terms "polypeptide" and "protein" are used interchangeably to refer to polymers of amino acids of any length, generally more than about 10, 20 or 30 amino acids. These terms also include proteins that are post-translationally modified through reactions that include glycosylation, acetylation and phosphorylation. The polypeptide may be a fusion polypeptide fused to fusion partner for half-life extension, such as Fc-fusions, albumin-fusions, or fusion partners as affinity tag for affinity chromatography, or fusion partners for providing correct N-termini or for increasing production yield of the protein of interest. The term "peptide" refers to shorter stretches of amino acids, generally less than about 30 amino acids. A polypeptide can serve as agonist or antagonist, and/or have therapeutic or diagnostic uses.

Further, a polypeptide expressed in a cell of the present invention can be of mammalian origin although microbial and yeast products can also be produced.

Examples of mammalian polypeptides or proteins include hormones, cytokines and lymphokines, antibodies such as Fabs, nanobodies, dAbs, scFvs, receptors, adhesion molecules, and enzymes as well as fragments thereof. A non-exhaustive list of desired products include, e. g., human growth hormone, bovine growth hormone, parathyroid hormone, thyroid stimulating hormone, follicle stimulating hormone growth, luteinizing hormone; hormone releasing factor; lipoproteins; alpha-1-antitrypsin; insulin A-chain; insulin B-chain; proinsulin; calcitonin; glucagon; molecules such as renin; clotting factors such as factor VIIIC, factor IX, tissue factor, and von Willebrands factor; anti-clotting factors such as Protein C, atrial natriuretic factor, lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A- or B-chain; prorelaxin; mouse gonadotropin-associated peptide; DNase; inhibin; activin; receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), growth factors including vascular endothelial growth factor (VEGF), nerve growth factor such as NGF-; platelet-derived growth factor (PDGF); fibroblast growth factor such as aFGF, bFGF, FGF-4, FGF-5, FGF-6; epidermal growth factor (EGF); transforming growth factor (TGF) such as TGF-alpha and TGF-beta, including TGF-pI, TGF-p2, TGF-p3, TGF-p4, or TGF-p5; insulin-like growth factor-I and -II (IGF-I and IGF-11); des (1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (Ls), e.g., IL-1 to IL-10; superoxide dismutase; erythropoietin; T-cell receptors; surface membrane proteins e.g., HER2; decoy accelerating factor; viral antigen such as, for example, a portion of the AIDS envelope; transport proteins; homing receptors; addressins; regulatory proteins; antibodies; chimeric proteins such as immunoadhesins and fragments of any of the above-listed polypeptides.

Preferred polypeptides and proteins herein are therapeutic proteins such as TGF-ß, TGF-α, PDGF, EGF, FGF, IGF-I, DNase, plasminogen activators such as t-PA, clotting factors such as tissue factor and factor VIII, hormones such as relaxin and insulin, cytokines such as IFN-y, chimeric proteins such as TNF receptor IgG immunoadhesin (TNFr-IgG) or antibodies such as bispecific antibodies, cameldid antibodies and fragments thereof, $V_{HH}$ domain antibodies, domain antibodies, immunoglobulins such as anti-IgG, anti-IgA, anti-IgM, anti-IgD or anti-IgE. Preferred therapeutic proteins are those of human origin or "humanized" proteins such as humanized antibodies as described herein.

If the product is a polypeptide, the polypeptide may be tagged, i.e., fused with a heterologous polypeptide which preferably allows isolation and/or purification of said polypeptide. The heterologous polypeptide can, for example, be a histidine tag, Flag-tag, streptavidin tag, strep II tag, an intein, maltose-binding protein, an IgA or IgG Fc portion, protein A or protein G.

If the product is a polynucleotide including a nucleotide sequence, the nucleotide sequence may be fused with a heterologous nucleotide sequence which allows isolation and/or purification of said expression product being a nucleotide sequence. For example, the heterologous nucleotide sequence can bind to a complementary nucleotide sequence, thereby allowing isolation and/or purification of said nucleotide sequence. "Heterologous" when used in the context of a heterologous polypeptide or nucleotide sequence means that a polypeptide or nucleotide sequence is different from the polypeptide or nucleotide sequence being the desired product.

If the product, as an example of a polynucleotide, is a plasmid, said plasmid is useful for gene therapy or DNA vaccination, or may encode a therapeutic protein, such as one described herein.

On the other hand, the cell may express a virus, i.e., the cell serves as producer cell line that provides, so to say, the appropriate environment that the virus replicates and/or is propagated. Accordingly, the product could be a virus. Virtually, any virus can be recovered by the methods of the present invention such as dsDNA viruses (e.g. Adenoviruses, Herpesviruses, Poxviruses), ssDNA viruses (e.g. Parvoviruses), dsRNA viruses (e.g. Reoviruses), (+) ssRNA viruses (e.g. Picornaviruses, Togaviruses), (−) ssRNA (e.g. Orthomyxoviruses, Rhabdoviruses), ssRNA-RT viruses (e.g. Retroviruses) and dsDNA-RT viruses (e.g. Hepadnaviruses). Viral replication is the term used to describe the formation of virus during the infection and propagation process in the target cells. From the perspective of the virus, the purpose of viral replication is to allow production and survival of its kind. By generating abundant copies of its genome and packaging these copies into viruses, the virus is able to continue infecting new hosts. In the context of the present invention it is preferred that viruses produced by appropriate host cells are not or essentially not capable of exiting the host cell, for example, by way of lysis or budding.

As mentioned before, the product may be a virus. A "virus" includes "native" viruses and "recombinant" viruses, with "native" meaning a virus which is isolated from nature and not genetically engineered (such as a clinical isolate) or a virus which can be found in nature (i.e., naturally-occurring) or a typical, established virus strain, for example used for immunization purposes (such as an attenuated virus).

The present invention thus provides a fast, efficient and inexpensive method which can be applied easily in industrial scale.

Uses of Positively Charged Microparticles and Negatively Charged Microparticles

In another aspect, the invention also relates to uses of the positively charged microparticles and negatively charged microparticles. Specifically, the invention provides a use of the positively charged microparticles and negatively charged microparticles or hydrophobic microparticles to adsorb molecules, preferably biomolecules, preferably proteins. Said proteins are preferably from cell homogenate or are from liquid culture medium of a cell expressing and secreting a protein of interest. The same embodiment is applicable to the hydrophobic microparticles.

The embodiments described in the context of the means and methods of the invention are equally applicable to the uses described above, mutatis mutandis.

Kit

The invention also provides a kit comprising the positively charged microparticles and negatively charged microparticles or the hydrophobic microparticles or both of the invention and optionally means for suspending said microparticles. The kit may contain for instance a centrifuge vial containing the microparticles.

The microparticles may be in the form of powder, or alternatively, in a liquid medium, such as in a slurry or a suspension. The microparticles are preferably not in the form of a gel. Furthermore, the kit may include a separate vial containing a desorption buffer.

The positively and negatively charged microparticles or hydrophobic microparticles of the present invention may be provided as a mixture or separately. In the latter, the positively charged microparticles and negatively charged microparticles are added to the biological fluids separately. They are not in contact with each other until both are added into the fluid. Therefore, the present invention also includes a biological fluid comprising positively charged microparticles and negatively charged microparticles.

EXAMPLES

Example 1

Preparation of Micro Particles from Ion Exchange Resins

Different types of ion exchange resins were purchased from Sigma Aldrich and DIAION®.

The following anion exchanger resins were used: AMBERLITE® IRA-400, AMBERLITE® IRA-743, DOWEX® 1X2-100, DOWEX® 1X2-400, DOWEX® 1X8-100, DOWEX® MARATHON® A2, DIAION® SA20A, DIAION® SA10A, DIAION® SA312

The following cation exchanger resins were used: DOWEX® 50 WX2-100, DOWEX® 50 WX8-100, MARATHON® C, DOWEX® MARATHON® MSC, DIAION® PK216, DIAION® SK110.

Resins were wet ground (20 g for ½ h) in a coated ceramic mortar by hand for ca. 30 min. Ground resins were suspended in water (ad 50 ml). After a period (ca. 96 h) supernatant of resins sediment was transferred to tubes. Supernatant was piecewise (1 ml) centrifuged for 15 min at 7000rcf (relative centrifugal force) until ca. 200 µl resin was collected per tube. Resins were re-suspended in 2M Sodium chloride (1.5 ml) an centrifuged for 1 min (7000rcf). Pellet of 1 min centrifugation was discarded (excepting AMBERLITE® IRA-743). Supernatant were transferred and centrifuged again for 15 min (7000rcf). Supernatant of 15 min centrifugation was discarded. Micro particles (ca. 200 µl) were also centrifuged in 2M Sodium chloride. Micro particles (ca. 150 µl) and other ground resins (50-200 µl) were re-suspended (1:4) in water and transferred in portions (50 µl resin) to tubes.

Aliquots of resin were centrifuged at 7000 rcf, supernatant was discarded and resin was re-suspended in 20 fold volume (about 1 ml) of aqueous washing solution. Time of incubation in solution was 30 min.

Wash sequence:
1×50% EtOH (dilution of organic residues)
3× deionized water (dilution of EtOH)
Check for near neutral pH
re-suspension of micro particles and ground resin in deionized water (about 70% v/v)
Resins were equilibrated in corresponding buffer used for specific experiments.

Determination of Particle Size Using Optical Microscopy

Particle size of the prepared microparticles was determined by optical microscopy using a software-based determination of size. Particle size of ground materials and micro particles was measured at 1000 fold magnification by estimation of relative diameter. Distribution was calculated by comparison of diameter sizes of 1000-5000 particles at 1% v/v. Results are shown in Table 1.

Morphology

AFM measurements were performed for visualization of the microparticles prepared from DOWEX® MARATHON® A2 and DOWEX® MARATHON® MSC. Samples were washed with ethanol and dried on a microscopic glass slide. For visualisation and analysis of data generated from AFM measurement the open source software Gwyddion (v 2.30) was used. Results are shown in FIG. 3-4. The ground microparticles are irregular in shape and no mesopores were observed.

Example 2

Preparation of Microparticles Using Laboratory Mill Ground by the Company NETZSCH DOWEX® MARATHON® MSC resin was wet ground using NETZSCH LabstarLS1 mill. 2 kg of resin were mixed with 3 kg water. After a period of about 200 minutes a $d_{50}$ of 1 µm was reached. The size distribution was analyzed during grinding with dynamic light scattering.

DOWEX® MARATHON® A2 resin was pre-ground by a coated ceramic mortar for 12 hours due to higher mechanical stability followed by wet grinding using NETZSCH LabstarLS1 mill.

In FIG. 5a-b, the size distribution as well as the mean diameter ($d_{50}$) of DOWEX® MARATHON® MSC is plotted against the duration of the grinding process. The size distribution during grinding spreads at the beginning, narrows from 200 minutes on and becomes monomodal at about 300 minutes. The mean diameter at this stage is about 300 nm. Grinding of DOWEX® MARATHON® MSC to an overall $d_{50}$ of 1-2 µm with a Labstar LS 1 mill always produces at least a bimodal distribution. At 200 minutes and at an overall $d_{50}$ of 1 µm the particle fraction with a $d_{50}$ of 1-2 µm is about 30%. Particles smaller than 1 µm account for about 55% whereas about 15% of the particles have a $d_{50}$ between 2 µm and 5 µm. Percentage is given as the ratio of the respective volumetric fractions(v/v). Grinding of

TABLE 1 lists resins used for preparation of microparticles.

| Type anion exchanger | Ligand | d (mm) | q BSA |
|---|---|---|---|
| AMBERLITE ® IRA-400 | —N$^+$—(CH$_3$)$_3$ (Type1) | 0.3-1.2 | 0.3 ± 0.11 |
| AMBERLITE ® IRA-743 | Methylglucamine | 0.5-0.7 | 6.1 ± 0.25 |
| DOWEX ® 1X2-100 | —N$^+$—(CH$_3$)$_3$ (Type1) | 0.1-0.5 | 0.5 ± 0.18 |
| DOWEX ® 1X2 -400 | —N$^+$—(CH$_3$)$_3$ (Type1) | 0.04-0.07 | 0.8 ± 0.01 |
| DOWEX ® 1X8-100 | —N$^+$—(CH$_3$)$_3$ (Type1) | 0.1-0.5 | 0.4 ± 0.03 |
| MARATHON ® A2 | —N$^+$—(CH$_2$—CH$_2$OH)—(CH$_3$)$_2$ (Type2) | 0.4-0.6 | 0.2 ± 0.02 |
| DIAION ® SA20A | Dimethylethanolamine | 0.3-1.18 | n.a. |
| DIAION ® SA10A | Trimethylamine | 0.3-1.18 | n.a. |
| DIAION ® SA312 | Trimethylamine | 0.3-1.18 | n.a. |

| Type cation exchanger | Ligand | d (mm) | |
|---|---|---|---|
| DOWEX ® 50 WX2-100 | —SO$_3^-$ | n.a. | n.a. |
| DOWEX ® 50 WX8-100 | —SO$_3^-$ | n.a. | n.a. |
| MARATHON ® C | —SO$_3^-$ | 1.2 | n.a. |
| MARATHON ® MSC | —SO$_3^-$ | 1.2 | n.a. |
| DIAION ® PK216 | Sulphonic | 0.3-1.18 | n.a. |
| DIAION ® SK110 | Sulphonic | 0.3-1.18 | n.a. |

A representative picture and evaluation for the anion exchanger DOWEX® 1X8-400 is shown in FIG. 1a-b. As shown in FIG. 2, a similar particle size range was obtained for all materials.

DOWEX® MARATHON® A2 with an LME30 mill to a $d_{50}$ of ~4 µm (5 mm beads) prior to grinding with a Labstar LMZ (2 mm beads) lead to a monomodal distribution with a $d_{50}$ of 1 µm.

Example 3

Kinetics of Adsorption of Microparticles

Aliquots of resin in ground form obtained from Dow were centrifuged at 7000 relative centrifugal force (rcf), supernatant was discarded and resin was re-suspended in tenfold volume (about 1 ml) of aqueous washing solution. Time of incubation in solution was 30 minutes. The washing was carried out as follows:

1×50% EtOH (dilution of organic residues)
3× deionized water (dilution of EtOH)
1×0.5M NaOH (substitution of anions to OH⁻)
4× deionized water (dilution of anions from interstitial fluid)
resuspension of microparticles in deionized water (about 20% v/v).

Kinetics of adsorption was determined by batch adsorption and drawing samples at distinct, very short time intervals. Stock solutions of Trypsin inhibitor (TI) and IgG were adjusted to about 5 mg Protein/ml in 20 mM Tris, pH 7.5. Further stock solution was diluted for each protein with buffer up to concentrations of 0.1 and 0.5 mg protein/ml. Microparticles (20% v/v) were diluted up to 4% v/v in 20 mM Tris, pH 7.5. Capacity of microparticles was estimated, and the amount of added microparticles was adjusted to adsorb half of protein amount at equilibrium. Final total volume of assay was 10 ml. This volume was split in two halves of 5 ml (first half containing protein and second half containing microparticles). The two halves were mixed in 0.25 ml portions in SpinX centrifugation tubes where incubation for different time intervals proceeded. After defined time intervals the mixture was filtered in order to stop adsorption of protein on microparticles. Amount of adsorbed protein was determined by measuring absorbance at 280 nm in micro well plates.

As shown in FIG. 4, the kinetics of adsorption was extremely fast. Almost 90% of the equilibrium capacity was reached within less than 10 seconds. Therefore, a difference between protein species could not be observed experimentally. Quantification by using appropriate adsorption models was also not possible. Conventional chromatography materials using similar experimental conditions show that equilibrium was not reached before a time period of 30 minutes up to 6 hours. This observation supports the findings of SEM measurements that the microparticles do not have mesopores.

Example 4

Equilibrium Capacity

Example 4.1

Microparticles prepared from example 1 are used to adsorb trypsin inhibitor (TI), bovine serum albumin (BSA), immunglobulin G (IgG), and green fluorescent protein (GFP). Equilibrium capacity and adsorption isotherms were evaluated. Stock solutions of trypsin inhibitor (TI), bovine serum albumin (BSA), immunglobulin G (IgG), green fluorescent protein (GFP) were adjusted to about 1 mg protein/ml. Adsorption conditions were: 20 mM Tris, pH 8.0 or 20 mM sodium acetate (NaAc) at pH 6.0. Ground resins (10% v/v) were added to each 1 ml protein solution and incubated at 20 rpm end-over-end at about 23° C. After 30 min samples of 1 ml were taken from tubes and 0.2 µm filtered. Amount of adsorbed protein was determined by measuring absorbance at 280 nm in micro well plates or in the case of GFP by fluorescence.

FIG. 6 shows the equilibrium capacities of the different anion exchange microparticles for trypsin inhibitor (FIG. 6a) and BSA (FIG. 6b). DIAION® SA20 and DIAION® PA312 show almost the same capacity, while capacity for DIAION® SA10 is lower.

FIG. 7 shows equilibrium capacities between the different cation exchange microparticles for lysozyme (FIG. 7a) and polyclonal IgG (FIG. 7b). NuviaS was included as a reference representing a conventional beaded material. The two cation exchangers DIAION® PK 216 and DIAION® SK110 have significantly lower capacities (15-25 mg/ml) compared to Dow resins (40-100 mg/ml) and also to Nuvia S (about 150 mg/ml).

FIG. 8 shows the equilibrium capacities of the different anion exchange microparticles for GFP from diafiltrated GFP homogenate. Capacities were almost equal for DOWEX® MARATHON® A2, DIAION® SA20 and DIAION® PA312 (40-50 mg GFP/ml) whereas DIAION® SA10 had a reduced capacity of ~20-25 mg/ml).

Example 4.2

The equilibrium capacity of DOWEX® MARATHON® MSC and NuviaS (Biorad) were evaluated at elevated salt levels (at conductivities between about 3.5 mS/cm and about 17 mS/cm). In contrast to NuviaS, the equilibrium capacity of polyclonal IgG for DOWEX® MARATHON® MSC remained nearly constant over the whole range of salt concentration. This shows that ground microparticles are therefore suited well for direct capture of IgG from cell culture supernatants. FIG. 9 shows the equilibrium capacities of polyclonal IgG plotted against the conductivity of the adsorption buffer for NuviaS resin (FIG. 9a) and DOWEX® MARATHON® MSC microparticles (FIG. 9b).

Example 5

Adsorption and Particle Size

The effect of particle size on equilibrium capacity was investigated. The microparticles are prepared in counter current flow or fractionated centrifugation to obtain microparticles of different sizes.

In FIG. 10, the capacity DOWEX® MARATHON® MSC for polyclonal IgG is plotted against the mean particle size ($d_{50}$). As shown, the capacity decreases drastically from a $d_{50}$ of 2 µm on, although microparticles smaller 1 µm would likely lead to a higher capacity. However, this limitation can be overcome by including oppositely-charged microparticles (as shown in Example 7)

Example 6

Adsorption/Desorption of GFP from E. coli Homogenate

Batch adsorption of recombinant GFP from E. coli homogenate were performed using DOWEX® MARATHON® A2 with the following steps.

Cell Disruption:

E. coli cell suspension was cooled overnight to 4° C. and centrifuged at 4000rcf and 4° C. for 15 min. Supernatant was discarded and pellet of cells was suspended in 50 mM Tris, pH 7.5, 50 mM NaCl to 165 g wet/kg (~30 g d.m./kg). Cells were disrupted by high pressure homogenization at 1000 bar by two passages. Homogenate was centrifuged at 10000rcf and 4° C. for 30 min and supernatant was filtered at 0.2 µm. Homogenate was diluted 1:5 with 50 mM Tris, pH 7.5, 50 mM NaCl and stored at 4° C.

Adsorption/Desorption

Batch adsorption/desorption was performed in tubes at small scale of 1 ml v at ~1 mg/ml C GFP on grinded DOWEX® MARATHON® A2 (chloride form) with 1.5 µm d50 (MA2). Start conductivity of homogenate was ~9 mS/cm. To 1 ml of homogenate 100 µl of 50% v/v MA2 were added. Samples were incubated for at least 15 min on a rotatory shaker. Afterwards samples were centrifuged at 7000rcf for 5 min (adsorption) or 15 min (desorption) and supernatant was transferred to other tubes. 1 ml of buffer was added to pellet and resin was suspended by vigorously mixing.

Protocols:
Adsorption
1 ml homogenate
1 ml 50 mM Tris, pH7.5
Elution
1 ml 50 mM Tris, pH7.5, 0.5M NaCl
Regeneration
1 ml 50 mM Tris, pH7.5, 1.0M NaCl
1 ml 50 mM Tris, pH7.5, 2.0M NaCl
Wash
3×1 ml ddH2O All steps were repeated three times without changing resin and tubes (pass 01-03).

Analysis
Green fluorescent protein (GFP), host cell protein (HCP) and double stranded DNA (ds DNA) were quantified by fluorescence (micro well plates), densitometry of SDS-Page (Silver and Coomassie staining) and Pico green assay (micro well plates).
Determination of GFP:
Samples were diluted 1:2, 1:4, 1:8 and 1:16 in micro well plates. Fluorescence was easured at 485 nm excitation and 535 nm emission. Concentration was determined with GFP standard calibration up to 18000FLU (about 80 µg GFP/ml).
Determination of Double-Stranded DNA (dsDNA):
Samples were diluted 1:2, 1:4, 1:8 and 1:16 in micro well plates. dsDNA was determined with Picogreen DNA assay by measuring fluorescence at 485 nm excitation and 535 nm emission. Concentration was determined with lambda dsDNA standard calibration up to 10000FLU (about 10 µg dsDNA/ml).
Determination of Endotoxins:
Endotoxins were measured by endpoint fluorometric analysis (PyroGene, rFC Endotoxin Detection System, Lonza).
Determination of HCP:
Electrophoresis samples were prepared by diluting (65%) in SDS Sample Buffer 4× (25%), 2 M DTT (10%) and heating at 100° C. for 10 min. Electrophoresis was performed in NuPage 10-20% acrylamide gel (200 V, 400 mA, 50 min) with MES-SDS running buffer. Protein was fixed on the gel with acid methanol solution for 10 min and stained with Coomassie-Bismarkbraun (Choi J-K, Yoon S-H, Hong H-Y, Choi D-K, Yoo G-S (1996) Anal Biochem 236:82). Optical density of staining was determined by densitometric analysis and calculated for each visible band of protein. Purity of GFP and amount of HCP, representing all other proteins, was estimated from this analysis.

Repeatability (3 times; Pass 01-03) of batch adsorption/desorption after non denaturing regeneration at high salt concentration for DOWEX® MARATHON® A2 microparticles was studied. The results are shown in FIG. 11a-c. While binding capacity of GFP and HCP doesn't change significantly between passes, that of ds DNA decrease steadily from pass 01 to pass 03. FIG. 11 shows the recovery (%) of GFP, HCP and ds DNA from ground DOWEX® MARATHON®A2 (MA2) after adsorption, elution and regeneration steps over pass 01, 02 and 03.

Elution fractions from self-made micro particles showed GFP recovery near 100% and at the same time about 60-70% of the host cell proteins (HCP) were removed. No double stranded DNA (dsDNA) was found in the eluates (ds DNA was recovered at high salt conditions c NaCl>1 M). Binding capacity of micro particles could not be restored completely by regenerating with 2M NaCl.

Endotoxine concentration for the supernatants during the adsorption/elution experiment was evaluated. Adsorption conditions were 20 mM Tris pH 7.5 and 100 mM NaCl. Elution was carried out at 20 mM Tris pH 7.5. Filtered cell homogenate was diluted 1:20 with 20 mM Tris pH 7.5 100 mM NaCl. Resulting GFP concentration was 0.5 mg/mL. The recovery of endotoxines from 100 µL DOWEX® MARATHON® A2 microparticles (MA2) during adsorption and elution is plotted in FIG. 12. A 5 log reduction was achieved up to salt levels of 1000 mM NaCl. The regeneration with 2 M NaCl was not studied.

Example 7.1

Adsorption of Polyclonal IgG

Polyclonal IgG was adsorbed on DOWEX® MARATHON® MSC at different pH values and salt concentrations (pH 5.0 and 6.0; 50 mM to 100 mM NaCl). Protein concentration was varied between 0.3 and 1.3 mg/mL DOWEX® MARATHON® MSC was used to adsorb polyclonal IgG as described in Example 4. Total solid concentration was varied between 0.5 and 2%. IgG concentration was varied between 0.2 mg/mL and 1.3 mg/mL. The adsorption conditions were either 20 mM sodium acetate at pH 5.0 or 20 mM MES at pH 6.0. Sodium chloride concentration was either 50 mM or 100 mM. Elution conditions were 20 mM sodium phosphate at pH 7.0 and 1 M NaCl. Sedimentation was conducted inside a mixed tank (EasyMax, Mettler Toledo). Sedimentation behavior was measured with an photocentrifuge (LumiSizer, L.U.M GmbH, Berlin).

Flocculation is formed after the adsorption step. Samples were taken with 5 mL Pipettes (minimum tip diameter of 3 mm). A typical example of flocculated DOWEX® MARATHON® MSC at 2% solid concentration is shown in FIG. 13.1.

The effect of adding DOWEX® MARATHON® A2 to DOWEX® MARATHON® MSC (Two Resin System; TRS) on the hydrodynamic diameter of formed flocs and thus on the normal distribution of the sttling velocity (at averaged 290 relative centrifugal forces) is further evaluated. FIG. 13.2 shows a boxplot of the 10% percentile (90% of the flocs are bigger) of the hydrodynamic diameter for different volumetric ratios of DOWEX® MARATHON® A2 to DOWEX® MARATHON® MSC. The effect of adding 10% DOWEX® MARATHON® A2 to DOWEX® MARATHON® MSC on the normal distribution of the settling velocity (at averaged 290 relative centrifugal forces) and the fitting parameters of a three parametric Gaussian curve is further evaluated. FIG. 14.1 shows a plot of the velocity distribution for flocculated DOWEX® MARATHON® MSC microparticles with fitted Gaussian curves. Flocculation was conducted with adsorbed polyclonal IgG alone (round symbols, dashed red line) and with additional 10% DOWEX® MARATHON® A2 (triangular symbols, solid green line). The mean settling velocity increased from 150 µm/s+/−39.0 up to 2874 µm/s+/−580.

DOWEX® MARATHON® A2 was added post adsorption. Data was recorded by a photo centrifuge (LumiSizer, L.U.M GmbH, Berlin) and analysed with the Software SepView (LumiSizer, L.U.M GmbH, Berlin). Stokes Law was used for calculating the hydrodynamic diameter. A density of 1.5 g/mL was assumed for the calculations. Plotting and fitting was done with the software matplotlib and scipy, respectively. Whiskers are plotted at 1.5 times the interquartile range. The inventors have therefore surprisingly found that by adding 10% DOWEX® MARATHON® A2, an increase by an order of magnitude in terms of hydrodynamic diameter was achieved. The median of the hydrodynamic diameter increased from 0.7 µm up to 40 µm. While the hydrodynamic diameter varies with varying process conditions, it remains in a precise range if the process conditions remain constant (which is the case at a ratio of 0.2).

Flocculation with microparticles of opposite charge could be done by adding the oppositely charged microparticles before or after the adsorption of protein. Due to the electrostatic interaction large flocs are formed.

The flocs formed between DOWEX® MARATHON® A2 and DOWEX® MARATHON® MSC can be easily resuspended by inverting the centrifuge tube.

It is found that If flocs were formed after the adsorption step, the DOWEX® MARATHON® A2 amount is preferably less than 20% to 30% DOWEX® MARATHON® A2. Otherwise DOWEX® MARATHON® A2 particles may remain un-flocculated.

Flocculating for 2 minutes or less at pH 6.0 and 100 mM NaCl seems to represent a preferable condition (in terms of settling velocity) for polyclonal IgG and DOWEX® MARATHON® MSC and 10% DOWEX® MARATHON® A2. The microparticles size may be between 0.1 µm and 2 µm ($d_{50}$). Under these conditions, a combination of high surface area and simple settling behavior can be achieved.

Example 7.2

Recovery and Purification of IgG from a CHO Cell Broth by Using Ground DOWEX® MARATHON® MSC and Ground DOWEX® MARATHON® A2

Loss of selectivity in applying the TRS (addition of ground DOWEX® MARATHON® A2 to ground DOWEX® MARATHON® MSC prior or post adsorption of IgG) can be avoided. If for example a positively charged protein (like IgG) is captured with a CIEX resin and the resin is subsequently flocculated with AIEX resin, impurities like DNA or HCP will bind too and eventually co-elute with the target protein. This effect can be observed in the case of IgG captured from CHO cell supernatant and DNA. IgG has a high affinity for the ion exchanger and therefore elutes only at high salt concentrations (1 M salt like NaCl). Unfortunately the DNA will co-elute at 1 M salt concentration FIG. 14.2 describes such a process. The pH of the cell supernatant was adjusted to 6.0 using 2 M HCl. Subsequently approximately 80 µl of a 50% (v/v packed bed) DOWEX® MARATHON® MSC suspension was added to 2 mL of the cell supernatant. After 2 minutes at 20 rpm on a rotary shaker between 8 µl and 40 µl DOWEX® MARATHON® A2 (v/v packed bed) was added. In other words, the volumetric ratio of DOWEX® MARATHON® A2 to DOWEX® MARATHON® MSC ranged from 10% to 50%. All microparticles were suspended in ultra pure water. The flocculated microparticles were separated by centrifugation at 1000 rcf for 5 minutes. The pellet was resuspended in 0.5 mL of 50 mM phosphate buffer at pH 7.0. The microparticles were separated by centrifugation at 1000 rcf for 5 minutes. Elution was carried out using 0.5 mL of 50 mM phosphate buffer at pH 7.0 containing 1 M NaCl. In all cases 60-80% of the DNA of the original CHO cell supernatant co-elutes with the IgG.

To circumvent the loss of selectivity prior to adsorption of IgG to ground DOWEX® MARATHON® MSC/ground DOWEX® MARATHON® A2 CHO cells are flocculated with AIEX microparticles. The cells can then be separated easily. It is possible to separate the flocculated cells by sedimentation or centrifugation at relative centrifugal forces between 5 g and 50 g within minutes. Impurities like DNA and other negatively charged proteins will bind to the AIEX resin. The flow chart in 14.3 describes this method. 350 µL of a 50% (v/v packed bed) DOWEX® MARATHON® A2 suspension was added to 10 mL of CHO supernatant. Below the chosen amount flocculation of CHO cells was incomplete and separation efficiency decreased. The formed flocs were then separated by centrifugation at relative centrifugal forces between 5 and 50 rcf. The capture and elution of IgG was carried out as described in the previous paragraph.

The obtained cell supernatant after flocculation of cells with ground DOWEX® MARATHON® A2 is nearly DNA free and at the same time approximately 60% of the host cell proteins were separated during the cell capture step. Overall, more than 87% of the host cell proteins could be separated. The results are summarized in Table 2.

TABLE 2

Measured concentration of IgG, DNA and host cell proteins during capture and elution according to FIG. 3. Concentrations were measured with following methods: IgG: SEC chromatography using UV detection at 280 nm. DNA: Picogreen assay (Invitrogen), host cell proteins: HCP - ELISA (Cygnus). Elution was carried out using 20 mM PO4 buffer containing 1M NaCl.

|  | Supernatant without cell flocculation | Supernatant after cell flocculation | Supernatant after IgG elution |
| --- | --- | --- | --- |
| IgG [mg/mL] | 1.0 | 1.0 | 5 or higher |
| DNA [ng/mL] | 1800 | 15 | below LOQ |
| HCP [µg/mL] | 155 | 58 | <20 |

Elution of IgG

Eluting IgG can be difficult due to its high affinity for DOWEX® MARATHON® MSC. The higher the affinity of the eluting ions for the ion exchanger, the less amounts are needed for complete recovery. Using 1 M KCl has a similar effect to using 1.5 M NaCl. More than 95 of the IgG could be recovered using 20 mM $PO_4$ buffer at pH 7.0 containing 1 M KCl. The results of elution experiments using DOWEX® MARATHON® MSC and monoclonal IgG are plotted in Error! Reference source not found.

Example 8

Comparison with Commercially Available Microspheres

Adsorption capacity of ground DOWEX® MARATHON® A2 and DOWEX® MARATHON® MSC were compared with cation exchanger CIEX (Polysciences POLYBEAD® Sulfate Microspheres 1.00 μm) and anion exchanger AIEX microspheres (ESTA[PR® Microspheres White Functionalized Microspheres K6-100) having similar functional groups. Particle sizes was determined by optical microscopy at 1000× magnification. Zeta potential was estimated in ddH20 at <0.1 mS/cm from electrophoretic mobility (based on Smoluchowski formula) measured by dynamic light scattering on a Malvern Zeta Sizer Nano series instrument.

As the figures show, these microspheres are similar in size (FIG. 15) and have similar zeta potential (FIG. 16).

GFP binding capacity was evaluated for AIEX microspheres and ground DOWEX® MARATHON® A2, whereas polyclonal IgG binding capacity was evaluated for and CIEX microspheres and ground DOWEX® MARATHON® MSC. Adsorption conditions were 50 mM TRIS at pH 8.0 and 50 mM MES at pH 6.0 for GFP and IgG, respectively. Equilibrium protein concentration was about 0.1 mg/ml resin The conditions as described in Example 4 were used to evaluate the binding capacity of GFP for AIEX (positively charged microparticles) and the binding capacity of polyclonal IgG.

While the ground microspheres are similar in size (see FIG. 15) and have similar zeta potential to the microspheres, their binding capacity is proved to be much higher than the commercially available microspheres. FIG. 17 shows that the protein binding capacity of ground microparticles is superior than commercial microspheres.

Example 9

Hydrophobic Microparticles

Preparation of Hydrophobic Microparticles

Adsorbent type resin provided by DOW: AMBERLITE® XAD4, AMBERLITE® XAD7HP and AMBERLITE® XAD761 were purchased from Sigma Aldrich, Vienna, Austria, 2011.

Resins were grinded overnight (20 g for ~12 h) with an electric motor driven, ceramic coated mortar. Grinded resins were suspended in water (~10% v/v and ad. 50 ml). Supernatant was centrifuged for 30 min at 4000×g (equivalent with relative centrifugal force). Resins were re-suspended in 2 M sodium chloride (50 ml) centrifuged for 1 min (4000× g). Pellet of 1 min centrifugation was discarded. Supernatant were transferred and centrifuged again for 30 min (4000×g). Supernatant was discarded. Grinded resins were re-suspended (1:2) in water and transferred to tubes. Resins were centrifuged at 4000×g, supernatant was discarded and resin was re-suspended in 50 ml of aqueous washing solution.

Wash sequence was:
1×50% EtOH (dilution of organic residues)
3× deionized water (dilution of EtOH)
Particle Size of Hydrophobic Microparticles Particle size distributions of microparticles were calculated from equivalent circular diameter by measurement of bright field microscopy projections of approximately 500 particles at 1% v/v and 600× fold magnification.

General Protocol for Microparticles and Conventional Chromatographic Media Adsorption/Desorption Adsorption and desorption studies were performed in 1 mL batches (homogenate or standard protein solution). Various amounts of 50% (v/v) microparticles suspensions (in μL), were added to protein solutions in 2 mL tubes. Dilution factor concerning protein concentration and conductivity was taken into account.

Microparticles suspensions were incubated for 30 minutes, conventional chromatographic media suspension for 12 hours. Afterwards microparticles or conventional chromatographic media were centrifuged at 7000×g for 10 min and elution of bound protein was performed by addition of 1 mL elution buffer, vigorous mixing and incubation for 30 min. In some cases a second washing step with elution buffer was included. After elution microparticles or conventional chromatographic media were centrifuged again as before. Concentration of protein in supernatants was quantified by photometric analysis and purity of target protein was checked by SDS-PAGE.

Example 10

Batch adsorption of recombinant GFP from E. coli homogenate was performed using positively charged microparticles (MPs) (ground chromatography resin DOWEX® MARATHON® A2 (MA2)) and negatively charged microparticles (MPs) (DOWEX® MARATHON® MSC (MMSC)) with the following steps. This example uses GFP as acidic intracellular soluble protein.

E. coli strain HMS174(DE3)(pET11aGFPmut3.1) was fermented in a 5 L scale fed-batch process. The expression of the intracellular soluble target protein GFP (green fluorescent protein) was induced using IPTG (Isopropyl β-D-1-thiogalactopyranoside).

Harvest and Homogenization: The E. coli suspension (biomass content ~30% wt) was cooled to 4° C. and centrifuged at 15000 g for 20 min. The supernatant was discarded and the cell pellet was further processed. The cell pellet was resuspended in 50 mM Tris, pH 7.5 and diluted to a biomass content 20% wt cells/buffer. Cells were disrupted by high pressure homogenization at 1000 bar for two passages producing the crude cell lysate.

For the batch adsorption from the lysate it is also possible to use frozen biomass. In this case the biomass (20% w/v) is resuspended in 50 mM Tris, pH 7.5, and same disruption procedures can also be applied as is the case for fresh fermented E. coli cells.

The batch adsorption was performed in tubes in small scale of 1 mL volume as well as in scales up to 100 mL in glass beakers at room temperature (rt). To the crude cell lysate MA2 was added (1.2 μL of 50% v/v MA2 were added per 1 μg cell pellet) and mixed for ~5 s in a lab vortex or in bigger scale with an overhead stirrer for ~30 s. During mixing the flocculation took place and the MA2 bound to the target protein as well as impurities like DNA, hcps (host cell proteins) and cell fragments. After the first flocculation negatively charged MPs were added (0.06 μL of DOWEX® MARATHON® MCS 50% v/v) to the mixture. Those counter charged MPs work as cross-linker that increases the particle size and stability of the flocculate. The flocculate can be centrifuged or filtrated.

For wash the pellet of the flocculate was resuspended in a 50 mM Tris wash buffer with 75 mM NaCl at pH 7.5. After short incubation the flocculate was separated using centrifugation (13400 g for 3 min). When the separation took place using a filtration process the filter cake was not resuspended but washed by filtrating the wash buffer through the filter cake (0.2 μm filter plate at 1.5 bar). The supernatant was discarded and the pellet/filter cake further processed for the elution step. The low salt concentration is able to elute impurities with low binding strength.

For the elution step the washed flocculate was resuspended in 50 mM Tris buffer containing 400 mM NaCl at pH 7.5. The flocculate was mixed in a tumbler for 5 min. At 400 mM NaCl concentration the target protein elutes from the MPs and is now in the supernatant. The supernatant was separated from the flocculate using centrifugation (13400 g for 3 min) or per dead-end filtration (0.2 µm filter plate at 1.5 bar). The pellet/filter cake containing the MPs with bound impurities was discarded and the supernatant containing the protein of interest (GFP) was processed further.

Example 11

Batch adsorption of recombinant GFP from E. coli homogenate is performed using positively charged microparticles (MPs) (ground chromatography resin DOWEX® MARATHON® A2 (MA2)) and negatively charged microparticles DOWEX® MARATHON® MSC (MMSC)) with the following steps. This example uses GFP as acidic intracellular soluble protein.

E. coli strain HMS174(DE3)(pET11aGFPmut3.1) is fermented in a 5 L scale fed-batch process. The expression of the intracellular soluble target protein GFP (green fluorescent protein) is induced using IPTG (Isopropyl β-D-1-thiogalactopyranoside).

Harvest and Homogenization: The E. coli suspension (biomass content ~30% wt) is cooled to 4° C. and centrifuged at 15000 g for 20 min. The supernatant is discarded and the cell pellet was further processed. The cell pellet is resuspended in 50 mM Tris, pH 7.5 and diluted to a biomass content 20% wt cells/buffer. Cells are disrupted by high pressure homogenization at 1000 bar for two passages producing the crude cell lysate.

For the batch adsorption from the lysate it is also possible to use frozen biomass. In this case the biomass (20% w/v) is resuspended in 50 mM Tris, pH 7.5, and same disruption procedures can also be applied as is the case for fresh fermented E. coli cells.

The batch adsorption is performed in tubes in small scale of 1 mL volume as well as in scales up to 100 mL in glass beakers at room temperature (rt). To the crude cell lysate MA2 was added (1.2 µL of 50% v/v MA2 were added per 1 µg wet cell pellet) and mixed for ~5 s in a lab vortex or in bigger scale with an overhead stirrer for ~30 s. During mixing the flocculation takes place and the MA2 binds the target protein as well as impurities like DNA, hcps (host cell proteins) and cell fragments. After the flocculation the samples are centrifuged for 3 min at 13400 g or filtrated using a 0.2 µm filter plate at 1.5 bar in a dead-end filtration with overhead pressure. The supernatant is discarded and the pellet/filter cake further processed for the wash step.

The cell pellet of the flocculate is resuspended in a 50 mM Tris wash buffer with 75 mM NaCl at pH 7.5. After short incubation the flocculate is separated using centrifugation (13400 g for 3 min). When the separation takes place using a filtration process the filter cake is not resuspended but washed by filtrating the wash buffer through the filter cake (0.2 µm filter plate at 1.5 bar). The supernatant was discarded and the pellet/filter cake further processed for the elution step. The low salt concentration is able to elute impurities with low binding strength.

For the elution step the washed flocculate is resuspended in 50 mM Tris buffer containing a salt concentration which is able to elute the target protein. The Suspension is now mixed with negatively charged microparticles to produce bigger more stable flocs. (0.06 µL of 50% v/v DOWEX® MARATHON® MSC per 1 µg of wet cell pellet) The target protein elutes from the MPs and is now in the supernatant. The supernatant can be separated from the flocculate using centrifugation or per dead-end filtration (0.2 µm filter plate at 1.5 bar). The pellet/filter cake containing the MPs with bound impurities can be discarded and the supernatant containing the protein of interest can be processed further.

Example 12

This example demonstrates the recovery of recombinant expressed basic proteins using MPs from ground DOWEX® MARATHON® A2 (MA2) resin from cell homogenate. The protein Interferon Gamma, IFN-γ, functions as an example for an intracellular soluble expressed basic protein. This example shows that the positively charged exchange resin can be used for biomolecule recovery by binding to unwanted cellular structures and intracellular material (referred to as negative purification).

IFN-γ was expressed intracellularly soluble in E. coli by fed-batch fermentation.

Harvest and Homogenization

Frozen biomass (20% w/v) of cells which express Interferon Gamma IFN-γ was used and resuspended in lysis buffer (20 mM Tris, 10 mM EDTA, 1 M Urea, 0.1% beta-mercaptoethanol). The cells were disrupted by high pressure homogenization at 950 bar for three passages producing the crude cell lysate. The cell disruption would also work with fresh biomass.

Negative Purification of the Target Protein

The batch adsorption was performed in tubes in small scale of 2 mL volume at room temperature (rt). The crude cell lysate was mixed with MA2 and mixed for ~5 s in a lab vortex (0.84 µL of 50% v/v DOWEX® MARATHON® A2 per 1 µg wet cell pellet). During mixing the flocculation takes place where MA2 binds negatively charged impurities like DNA, hcps (host cell proteins) and cell fragments.

After the first flocculation the counter charged MPs are added (0.042 µL of 50% v/v DOWEX® MARATHON® MSC per 1 µg wet cell pellet) to the mixture and a second mixing step is performed. Those oppositely charged MPs work as cross-linker that increases the particle size and stability of the flocculate. The flocculate can be centrifuged or filtrated. The pellet/filter cake containing the MPs with bound impurities can be discarded and the supernatant containing the protein of interest can be processed further.

Example 13

This example shows the extraction of an acidic charged intracellular recombinant protein from intact E. coli cells using positively and negatively charged MPs (MA2 and MMSC).

E. coli strains HMS174(DE3)(pET11aGFPmut3.1) and BL21(pBI1KT7ix.1_GFP.1) are fermented in a 5 L scale fed-batch process. The expression of the intracellular soluble target protein GFP (green fluorescent protein) is induced using IPTG (Isopropyl β-D-1-thiogalactopyranoside).

The cells are harvested and stored overnight (~12 h) at 4° C. in FLEXBOY® Bags. The E. coli suspension (biomass content ~30% wt) is cooled to 4° C. and centrifuged at 15000 g for 20 min and later resuspended with a 50 mM Tris buffer at pH 7.5 while containing the same biomass content.

Cell Flocculation and Protein Extraction

For the first flocculation positively charged MPs are added to the cell suspension (102 µL MA2 (50% v/v) per 1 mL cell suspension at 30% wet biomass content) to bind and flocculate the *E. coli* cells. While the MPs are in contact with the cells the extraction takes place and the target protein (here GFP) will accumulate in the supernatant. After an incubation of 2-3 h the extraction is complete and the negatively charged MPs (negatively charged DOWEX® MARATHON® MSC: 5.4 μL per 1 mL cell suspension at 30% wet biomass content) are added to the flocculated cells. The particle size of the flocculate increases and the stability of the flocculate is increased. After the second flocculation step the flocculate can be separated using filtration or centrifugation. The cell pellet/filter cake was discarded and the supernatant containing the target protein was further processed.

After the first addition of positively charged MPs the supernatant has a milky-turbidity which originates from unbound MPs (in this case MA2). Once the oppositely charged MPs (MMSC) are added to the mixture the turbidity vanishes which demonstrates the second flocculation step. The cells bound to the MA2-MPs which are stabilized by the counter-charged MPs (MMSC).

Example 14

Extraction of GFP is performed using positively charged MPs (DIAION® SA20A) and negatively charged MPs (DOWEX® 50WX2-100)

Positively charged MPs is prepared from DIAION® SA20A and negatively charged MPs is prepared from DOWEX® 50WX2-100 as described in Example 1.

*E. coli* strains HMS174(DE3)(pET11aGFPmut3.1) and BL21(pBI1KT7ix.1_GFP.1) are fermented in a 5 L scale fed-batch process. The expression of the intracellular soluble target protein GFP (green fluorescent protein) is induced using IPTG (Isopropyl β-D-1-thiogalactopyranoside).

The cells are harvested and stored overnight (~12 h) at 4° C. in FLEXBOY® Bags. The *E. coli* suspension (biomass content ~30% wt) is cooled to 4° C. and centrifuged at 15000 g for 20 min and later resuspended with a 50 mM Tris buffer at pH 7.5 while containing the same biomass content.

For the first flocculation the positively charged MPs are added to the cell suspension to bind and flocculate the *E. coli* cells. While the MPs are in contact with the cells the extraction takes place and the target protein (here GFP) will accumulate in the supernatant. After an incubation of 2-3 h the extraction is complete and the negatively charged MPs are added to the flocculated cells. The particle size of the flocculate increases and the stability of the flocculate is increased. After the second flocculation step the flocculate can be separated using filtration or centrifugation. The cell pellet/filter cake was discarded and the supernatant containing the target protein was further processed.

Example 15

Extraction of GFP is performed using positively charged MPs (DIAION® SA312) and negatively charged MPs (DOWEX® 50WX8-100)

Positively charged MPs is prepared from DIAION® SA312 and negatively charged MPs is prepared from DOWEX® 50WX8-100 as described in Example 1.

*E. coli* strains HMS174(DE3)(pET11aGFPmut3.1) and BL21(pBI1KT7ix.1_GFP.1) are fermented in a 5 L scale fed-batch process. The expression of the intracellular soluble target protein GFP (green fluorescent protein) is induced using IPTG (Isopropyl β-D-1-thiogalactopyranoside).

The cells are harvested and stored overnight (~12 h) at 4° C. in FLEXBOY® Bags. The *E. coli* suspension (biomass content ~30% wt) is cooled to 4° C. and centrifuged at 15000 g for 20 min and later resuspended with a 50 mM Tris buffer at pH 7.5 while containing the same biomass content.

For the first flocculation the positively charged MPs are added to the cell suspension to bind and flocculate the *E. coli* cells. While the MPs are in contact with the cells the extraction takes place and the target protein will accumulate in the supernatant. After an incubation of 2-3 h the extraction is complete and the negatively charged MPs are added to the flocculated cells. The particle size of the flocculate increases and the stability of the flocculate is increased. After the second flocculation step the flocculate can be separated using filtration or centrifugation. The cell pellet/filter cake was discarded and the supernatant containing the target protein was further processed.

Example 16

Comparison of the Binding Capacity of Polyclonal IgG on Ground DOWEX® MARATHON® MSC and a Mixture of Ground DOWEX® MARATHON® MSC and Ground DOWEX® MARATHON® A2

Polyclonal IgG was adsorbed on ground DOWEX® MARATHON® MSC (d50=1 μm) at 50 mM MES pH 6.0 containing 50 mM and 100 mM NaCl, respectively. In one case the resin was flocculated with ground DOWEX® MARATHON® A2 prior to the adsorption step (Two Resin System; TRS). In the other case only DOWEX® MARATHON® MSC was used for protein adsorption (One Resin System; ORS). The ratio of DOWEX® MARATHON® A2 to DOWEX® MARATHON® MSC was adjusted to 0.4. Other ratios ranging from 0.01 to 0.99 are also possible. Adsorption was conducted for 15 minutes on a rotary shaker. Subsequently the particles were separated by centrifugation. A following filtration step, using a syringe filter with a pore width of 0.2 μm, was carried out in order to ensure that no particles interfere with the protein measurements. Protein concentration was determined via UV adsorption at 280 nm in microtiter plates. The results are plotted in FIG. 18.

Protein capacity between using ORS and TRS is comparable. The flocculation prior to the adsorption of polyclonal IgG does not decrease the maximum protein capacity for polyclonal IgG.

Polyclonal IgG used: Octagam 5% (Octapharma AG). Solutions were prepared by diluting the 5% solution with corresponding buffer.

The invention claimed is:

1. A composition consisting essentially of positively charged microparticles and negatively charged microparticles,
   wherein the positively charged microparticles comprise a ground polymeric anion-exchange resin, and wherein the negatively charged microparticles comprise a ground polymeric cation exchange resin,
   wherein the anion-exchange resin and the cation exchange resin are polystyrene-based, Hydroxyethyl methacrylate (HEMA)-based, dimethylamino ethylmethacrylate (DMAEMA)-based, dimethylamino ethylmethacrylate (pDMAEMA), or methacrylic acid (MAA)-based, and
   wherein the microparticles have an average particle size of less than about 5 μm.

2. The composition of claim 1, wherein the cation exchange resin is weakly or strongly acidic.

3. The composition of claim 1, wherein the anion-exchange resin is weakly or strongly basic.

4. The composition of claim 1, wherein the cation exchange resin and anion-exchange resin are polystyrene cross-linked with divinylbenzene-based.

5. The composition of claim 1, wherein the anion-exchange resin is AMBERLITE® IRA-485, AMBERLITE® IRA-400, DOWEX® 1X2-100, DOWEX® 1-8-100, DOWEX® MARATHON® A2 or DIAION® SA 20A.

6. The composition of claim 1, wherein the cation exchange resin is AMBERLITE® IRC-748, DOWEX® 50 WX2-100, DOWEX® 50 WX8-100, DOWEX® MARATHON® MSC or DIAION® SK 110.

7. A method of obtaining a biomolecule from a biological fluid comprising said biomolecule comprising:
   a) adding positively charged microparticles comprising a ground polymeric anion-exchange resin and adding negatively charged microparticles comprising a ground polymeric cation-exchange resin to the biological fluid,
   b) allowing the microparticles to form flocs,
   c) removing the flocs from the biological fluid, and
   d) recovering the biomolecule;
   wherein the anion-exchange resin and the cation exchange resin are polystyrene-based, Hydroxyethyl methacrylate (HEMA)-based, dimethylamino ethylmethacrylate (DMAEMA)-based, dimethylamino ethylmethacrylate (pDMAEMA), or methacrylic acid (MAA)-based.

8. The method of claim 7, wherein the cation exchange resin is weakly or strongly acidic.

9. The method of claim 7, wherein the anion-exchange resin is weakly or strongly basic.

10. The method of claim 7, wherein the cation exchange resin and anion-exchange resin are polystyrene cross-linked with divinylbenzene-based.

11. The method of claim 7, wherein the microparticles have an average particle size of less than about 5 μm.

12. The method of claim 7, wherein the anion-exchange resin is AMBERLITE® IRA-485, AMBERLITE® IRA-400, DOWEX® 1X2-100, DOWEX® 1-8-100, DOWEX®MARATHON®A2 or DIAION® SA 20A.

13. The method of claim 7, wherein the cation exchange resin is AMBERLITE® IRC-748, DOWEX® 50 WX2-100, DOWEX® 50 WX8-100, DOWEX® MARATHON® MSC or DIAION® SK 110.

14. The method of claim 7, wherein the biomolecule is a protein or a plasmid.

15. The method of claim 7, wherein the biological fluid is a cell homogenate or a fermentation supernatant.

16. The method of claim 7, wherein the biological fluid comprises cells and the microparticles disrupt the cells or extract the biomolecule from the cells.

17. The method of claim 16, wherein the microparticles adsorb the biomolecule.

18. A composition comprising
   (a) a biological fluid comprising biomolecules,
   (b) positively charged microparticles comprising a ground polymeric anion-exchange resin, and
   c) negatively charged microparticles comprising a ground polymeric cation-exchange resin; and
   wherein the microparticles have an average particle size of less than about 5 μm.

* * * * *